(12) United States Patent
Liang et al.

(10) Patent No.: US 11,220,502 B2
(45) Date of Patent: Jan. 11, 2022

(54) SULFONE COMPOUNDS AND DERIVATIVES FOR THE TREATMENT AND PROPHYLAXIS OF VIRUS INFECTION

(71) Applicant: Hoffmann-La Roche Inc., Little Falls, NJ (US)

(72) Inventors: Chungen Liang, Shanghai (CN); Jianping Wang, Shanghai (CN); Hongying Yun, Shanghai (CN); Kun Miao, Shanghai (CN)

(73) Assignee: Hoffmann-La Roche, Inc., Little Falls, NJ (US)

( * ) Notice: Subject to any disclaimer, the term of this patent is extended or adjusted under 35 U.S.C. 154(b) by 0 days.

(21) Appl. No.: 16/990,858

(22) Filed: Aug. 11, 2020

(65) Prior Publication Data
US 2020/0369664 A1 Nov. 26, 2020

Related U.S. Application Data

(63) Continuation of application No. PCT/EP2019/053232, filed on Feb. 11, 2019.

(30) Foreign Application Priority Data

Feb. 12, 2018 (WO) ................ PCT/CN2018/076525

(51) Int. Cl.
*C07D 473/24* (2006.01)
(52) U.S. Cl.
CPC .................................. *C07D 473/24* (2013.01)
(58) Field of Classification Search
None
See application file for complete search history.

(56) References Cited

U.S. PATENT DOCUMENTS

| | | | |
|---|---|---|---|
| 7,642,350 B2 | 1/2010 | Pryde et al. | |
| 9,556,176 B2 | 1/2017 | Bonfanti et al. | |
| 9,708,325 B2 | 7/2017 | Liang et al. | |
| 10,233,184 B2 | 3/2019 | Gao et al. | |
| 2006/0052403 A1 | 3/2006 | Isobe et al. | |
| 2010/0143301 A1 | 6/2010 | Desai et al. | |
| 2011/0098248 A1 | 4/2011 | Halcomb et al. | |
| 2011/0150836 A1 | 6/2011 | Halcomb et al. | |
| 2016/0326177 A1 | 11/2016 | Liang et al. | |
| 2017/0275286 A1 | 9/2017 | Liang et al. | |
| 2018/0072730 A1 | 3/2018 | Gao et al. | |
| 2019/0185469 A1 | 6/2019 | Dyckman et al. | |
| 2019/0256515 A1 | 8/2019 | Gao et al. | |
| 2020/0109144 A1 | 4/2020 | Liang et al. | |
| 2020/0268762 A1 | 8/2020 | Poeschinger et al. | |
| 2020/0385387 A1 | 12/2020 | Gao et al. | |

FOREIGN PATENT DOCUMENTS

| | | |
|---|---|---|
| CN | 101239980 A | 8/2008 |
| EA | 021463 B1 | 6/2015 |
| EP | 2476682 A1 | 7/2012 |
| JP | 11-193282 A | 7/1999 |
| JP | 2014-076947 A1 | 5/2014 |
| WO | 98/01448 | 1/1998 |
| WO | 99/28320 A1 | 6/1999 |
| WO | 99/32122 | 7/1999 |
| WO | 2006/117670 A1 | 11/2006 |
| WO | 2008/0055555 A1 | 1/2008 |
| WO | 2009/005687 A1 | 1/2009 |
| WO | 2014/154859 A1 | 10/2014 |
| WO | 2015/057655 A1 | 4/2015 |
| WO | 2015/057659 A1 | 4/2015 |
| WO | 2016/023511 A1 | 2/2016 |
| WO | 2016/180695 A1 | 11/2016 |
| WO | 2019/028302 A1 | 2/2017 |
| WO | 2017/106607 A1 | 6/2017 |
| WO | 2018/005586 A1 | 1/2018 |
| WO | 2018/026620 A1 | 2/2018 |
| WO | 2018/031434 A1 | 2/2018 |
| WO | 2018/041763 A1 | 3/2018 |
| WO | 2018/047081 A1 | 3/2018 |
| WO | 2018/049089 A1 | 3/2018 |
| WO | 2018/050571 A1 | 3/2018 |

(Continued)

OTHER PUBLICATIONS

Alper et al., "Discovery of potent, orally bioavailable in vivo efficacious antagonists of the TLR7/8 pathway" Bioorg. Med. Chem. Lett. 30(127366):1-5 ( 2020).
Asselah, T., et al., "Interferon therapy for chronic hepatitis B" Clin Liver Dis 11(4):839-849 (Nov. 1, 2007).
Connolly, D., et al., "New developments in Toll-like receptor targeted therapeutics" Curr Opin Pharmacol 12(4):510-518 (Aug. 1, 2012).
Gane, E., et al., "Safety and pharmacodynamics of oral TLR-7 agonist GS-9620 in patients with chronic hepatitis B" Abstract Ann. Meeting Am. Assoc. Study Liver Dis, Washington, D.C., pp. 661A, Abstract 946 ( Nov. 2013).

(Continued)

*Primary Examiner* — Craig D Ricci
(74) *Attorney, Agent, or Firm* — Genentech, Inc.; Richard G. A. Bone

(57) ABSTRACT

The present invention relates to compounds of formula (I),

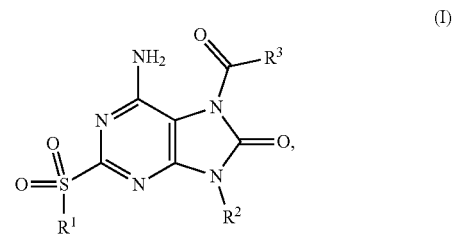

(I)

wherein $R^1$, $R^2$ and $R^3$ are as described herein, and their prodrugs or pharmaceutically acceptable salts, enantiomers or diastereomers thereof, and compositions including the compounds and methods of using the compounds.

14 Claims, No Drawings

(56) References Cited

FOREIGN PATENT DOCUMENTS

| WO | 2019/018354 A1 | 1/2019 |
| WO | 2019/028301 A1 | 2/2019 |
| WO | 2019/099336 A1 | 5/2019 |
| WO | 2019/118799 A1 | 6/2019 |
| WO | 2019/123294 A2 | 6/2019 |
| WO | 2019/125849 A1 | 6/2019 |
| WO | 2019/126082 A1 | 6/2019 |
| WO | 2019/126083 A1 | 6/2019 |
| WO | 2019/126113 A1 | 6/2019 |
| WO | 2019/126242 A1 | 6/2019 |
| WO | 2019/126253 A1 | 6/2019 |
| WO | 2019/220390 A1 | 11/2019 |

OTHER PUBLICATIONS

Hemmi, H., et al., "Small anti-viral compounds activate immune cells via the TLR7 MyD88-dependent signaling pathway" Nat Immunol 3(2):196-200 (Jan. 22, 2002).

International Preliminary Report on Patentability for PCT/EP2019/053232 dated Aug. 28, 2020.

International Search Report and Written Opinion for PCT/EP2019/054729 dated Jun. 5, 2019.

International Search Report for PCT/EP2019/053232 dated Apr. 26, 2019.

Kaisho, T., et al., "Turning NF-kB and IRFs on and off in DC" Trends Immunol 29(7):329-336 (Jul. 1, 2008).

Knoepfel et al., "Target-Based Identification and Optimization of 5-Indazol-5-yl Pyridones as Toll-like Receptor 7 and 8 Antagonists Using a Biochemical TLR8 Antagonist Competition Assay" J. Med. Chem. 63:8276-8295 ( 2020).

Kurimoto, A., et al., "Prodrugs of 9-Benzyl-8-hydroxy-2-(2-hydroxyethylthio)adenine: Potent Interferon Inducing Agents in Monkeys" Chem Pharm Bull (Tokyo) 52(4):466-469 (Apr. 1, 2004).

Lamphier, M., et al., "Novel Small Molecule Inhibitors of TLR7 and TLR9: Mechanism of Action and Efficacy In Vivo" Mol Pharmacol 85(3):429-440 (Mar. 1, 2014).

Mussari et al., "Discovery of Potent and Orally Bioavailable Small Molecule Antagonists of Toll-like Receptors 7/8/9 (TLR7/8/9)" ACS Med. Chem. Lett. 11:1751-1758 ( 2020).

Roethle, P., et al., "Identification and Optimization of Pteridinone Toll-like Receptor 7 (TLR7) Agonists for the Oral Treatment of Viral Hepatitis" J Med Chem 56(18):7324-7333 (Sep 26, 2013).

Saal, C., et al., "Pharmaceutical salts: A summary on doses of salt formers from the Orange Book" Eur J Pharm Sci 49(4):614-623 (Jul. 16, 2013).

Sepehri, Z., et al., "The link between TLR7 signaling and hepatitis B virus infection" Life Sci 158:63-69 (Aug. 1, 2016).

Verweij Intertantional Library of Ethics, Law, and the New Medicine "Preventive Medicine Between Obligation and Aspiration"Springer-Science + business Media, B.V., vol. 4 ( 2013).

Zawilska, J., et al., "Prodrugs: A challenge for the drug development" Pharmacol Rep 65(1):1-14 (Jan. 1, 2013).

SULFONE COMPOUNDS AND DERIVATIVES FOR THE TREATMENT AND PROPHYLAXIS OF VIRUS INFECTION

CROSS-REFERENCE TO RELATED APPLICATIONS

This application is a Continuation of International Application No. PCT/EP2019/053232, filed Feb. 11, 2019, which claims benefit of priority to Chinese Patent Application No. PCT/CN2018/076525 filed Feb. 12, 2018, each of which is incorporated herein by reference in its entirety.

TECHNICAL FIELD

The present invention relates to novel sulfonimidoylpurinones derivatives that have in vivo Toll-like receptor agonism activity, as well as their manufacture, pharmaceutical compositions containing them and their potential use as medicaments.

The present invention relates to compounds of formula (I),

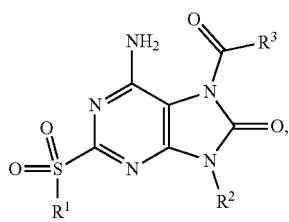

wherein $R^1$ to $R^3$ are described below, or a pharmaceutically acceptable salt, enantiomer or diastereomer thereof.

BACKGROUND

Toll-like receptors (TLRs) detect a wide range of conserved pathogen-associated molecular patterns (PAMPs). They play an important role of sensing invading pathogens and subsequent initiation of innate immune responses. There are 10 known members of the TLR family in human, which are type I transmembrane proteins featuring an extracellular leucine-rich domain and a cytoplasmic tail that contains a conserved Toll/interleukin (IL)-1 receptor (TIR) domain. Within this family, TLR3, TLR7, TLR8 and TLR9 are located within endosomes. TLR7 can be activated by binding to a specific small molecule ligand (i.e., TLR7 agonist) or its native ligand (i.e., single-stranded RNA, ssRNA). Following binding of ssRNA to TLR7, the receptor in its dimerized form is believed to undergo a structural change leading to the subsequent recruitment of adapter proteins at its cytoplasmic domain, including the myeloid differentiation primary response gene 88 (MyD88). Following the initiation of the receptor signalling cascade via the MyD88 pathway, cytoplasmic transcription factors such as interferon regulatory factor 7 (IRF-7) and nuclear factor kappa B (NF-κB) are activated. These transcription factors then translocate to the nucleus and initiate the transcription of various genes, e.g., IFN-α and other antiviral cytokine genes. TLR7 is predominately expressed on plasmacytoid cells, and also on B-cells. Altered responsiveness of immune cells might contribute to the reduced innate immune responses during chronic viral infections. Agonist-induced activation of TLR7 might therefore represent a novel approach for the treatment of chronic viral infections. (D. J Connolly and L. AJ O'Neill, Current Opinion in Pharmacology 2012, 12:510-518, P. A. Roethle et al, J. Med. Chem. 2013, 56, 7324-7333).

The current therapy of chronic HBV infection is based on two different types of drugs: the traditional antiviral nucleos(t)ide analogues and the more recent Pegylated IFN-α (PEG-IFN-α). The oral nucleos(t)ide analogues act by suppressing the HBV replication. This is a life-long course of treatment during which drug resistance often occurs. As an alternative option, Pegylated IFN-α (PEG-IFN-α) has been used to treat some chronic infected HBV patients within finite therapy duration. Although it has achieved seroconversion in HBeAg at least in a small percentage of HBV patients, the adverse effect makes it poorly tolerable. Notably, functional cure defined as HBsAg seroconversion is very rare with both current therapies. A new generation therapeutic option to treat HBV patients for a functional cure is therefore of urgent need. Treatment with an oral TLR7 agonist represents a promising solution to provide greater efficacy with better tolerability. Pegylated IFN-α (PEG-IFN-α) is currently used to treat chronic HBV and is an alternative to potentially life-long treatment with antiviral nucleos(t)ide analogues. In a subset of chronic HBV patients, PEG-IFN-α therapy can induce sustained immunologic control of the virus following a finite duration of therapy. However, the percentage of HBV patients that achieve seroconversion with interferon therapy is low (up to 27% for HBeAg-positive patients) and the treatment is typically poorly tolerated. Furthermore, functional cure (defined as HBsAg loss and seroconversion) is also very infrequent with both PEG-IFN-α and nucleos(t)ide treatment. Given these limitations, there is an urgent need for improved therapeutic options to treat and induce a functional cure for chronic HBV. Treatment with an oral, small-molecule TLR7 agonist is a promising approach that has the potential to provide greater efficacy and tolerability (T. Asselah et al, Clin Liver Dis 2007, 11, 839-849).

In fact, several identified TLR7 agonists have been considered for therapeutic purposes. So far Imiquimod (ALDARA™) is a U.S. FDA approved TLR7 agonist drug for topical use to treat skin lesions by human papillomavirus. The TLR7/8 dual agonist resiquimod (R-848) and the TLR7 agonist 852A have been evaluated for treating human genital herpes and chemotherapy-refractory metastatic melanoma, respectively. ANA773 is an oral pro-drug TLR7 agonist, developed for the treatment of patients with chronic hepatitis C virus (HCV) infection and chronic hepatitis B infection. GS-9620 is an orally available TLR7 agonist. A phase Ib study demonstrated that treatment with GS-9620 was safe, well tolerated and resulted in dose-dependent ISG15 mRNA induction in patients with chronic hepatitis B (E. J. Gane et al, Annu Meet Am Assoc Study Liver Dis (November 1-5, Washington, D.C.) 2013, Abst 946). Therefore there is high unmet clinical need for developing potent and safe TLR7 agonists as new HBV treatment to offer more therapeutic solutions or replace existing partly effective treatment.

SUMMARY

The present invention provides a series of novel sulfone compounds that have Toll-like receptor agonism activity. The invention also provides the bio-activity of such compounds to induce SEAP level increase by activating Toll-like receptors, such as TLR7 receptor, the metabolic conversion of prodrugs to parent compounds in the presence of human hepatocytes, and the therapeutic or prophylactic use of such compounds and their pharmaceutical compositions comprising these compounds as the prodrugs to treat or prevent infectious disease like HBV or HCV. This invention leads us to a new finding that local activation of TLR7 in GALT is more likely to limit tolerability, and the issue can be overcome with prodrugs disclosed hereof. Therefore a series of unusual and rare urea prodrugs were discovered to be pharmacologically inactive, stable in GI and rapid conversion to parent in liver, which showed in vivo Toll-like receptor agonism activity and potentially useful for the treatment and prophylaxis of HBV infection. The present invention also provides compounds with superior activity. In addition, the compounds of formula (I) also show good solubility and PK profiles.

The present invention relates to novel compounds of formula (I),

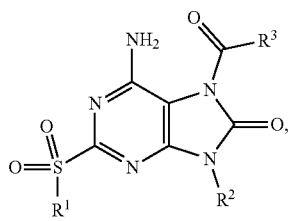

wherein:

$R^1$ is $C_{1-6}$ alkyl;

$R^2$ is phenyl $C_{1-6}$ alkyl, said phenyl being unsubstituted or substituted by one, two or three substituents independently selected from halogen, $C_{1-6}$ alkoxy and $C_{1-6}$ alkyl;

$R^3$ is —$NR^4R^5$, wherein $R^4$ and $R^5$ are independently selected from $C_{1-6}$ alkyl or $C_{1-6}$ alkoxy $C_{1-6}$ alkyl; or $R^4$ and $R^5$ together with the nitrogen they are attached to form a heterocyclyl;

or a pharmaceutically acceptable salt, enantiomer or diastereomer thereof.

The invention also relates to their manufacture, medicaments based on a compound in accordance with the invention and their production as well as the use of compounds of formula (I) thereof as TLR7 agonist. Accordingly, the compounds of formula (I) are useful for the treatment or prophylaxis of HBV and/or HCV infection with Toll-like receptors agonism.

DETAILED DESCRIPTION

Unless otherwise defined, all technical and scientific terms used herein have the same meaning as commonly understood by one of ordinary skill in the art to which this invention belongs. Furthermore, the following definitions are set forth to illustrate and define the meaning and scope of the various terms used to describe the invention.

Definitions

The term "$C_{1-6}$ alkyl" denotes a saturated, linear or branched chain alkyl group containing 1 to 6, particularly 1 to 4 carbon atoms, for example methyl, ethyl, n-propyl, isopropyl, n-butyl, isobutyl, tert-butyl and the like. Particular "$C_{1-6}$ alkyl" groups are methyl, ethyl and n-propyl.

The term "$C_{1-6}$ alkoxy" denotes a group of the formula $C_{1-6}$ alkyl—O—. Examples of $C_{1-6}$ alkoxy group include, but not limited to, methoxy, ethoxy, n-propoxy, isopropoxy, n-butoxy, isobutoxy and tert-butoxy. Particular "$C_{1-6}$ alkoxy" groups are methoxy, ethoxy and isopropoxy. A more particular $C_{1-6}$ alkoxy group is ethoxy.

The terms "halogen" and "halo" are used interchangeably herein and denote fluoro, chloro, bromo, or iodo.

The term "heterocyclyl" denotes a monovalent saturated or partly unsaturated mono or bicyclic ring system of 3 to 10 ring atoms, comprising 1 to 5 ring heteroatoms selected from N, O and S, the remaining ring atoms being carbon. In particular embodiments, heterocyclyl is a monovalent saturated monocyclic ring system of 4 to 7 ring atoms, comprising 1, 2, or 3 ring heteroatoms selected from N, O and S, the remaining ring atoms being carbon. Examples for monocyclic saturated heterocyclyl are aziridinyl, oxiranyl, azetidinyl, oxetanyl, pyrrolidinyl, dimethylpyrrolidinyl, ethoxycarbonylpyrrolidinyl, tetrahydrofuranyl, tetrahydrothienyl, pyrazolidinyl, imidazolidinyl, oxazolidinyl, isoxazolidinyl, thiazolidinyl, piperidinyl, tetrahydropyranyl, tetrahydrothiopyranyl, piperazinyl, morpholinyl, thiomorpholinyl, dioxothiomorpholinyl, azepanyl, diazepanyl, homopiperazinyl, or oxazepanyl. Monocyclic saturated heterocyclyl can be further substituted by one to three substituents independently selected from halogen, $C_{1-6}$ alkyl and $C_{1-6}$ alkoxycarbonyl. Examples for substituted monocyclic saturated heterocyclyl are 4-methylpiperazinyl, dimethylpyrrolidinyl, ethoxycarbonylpyrrolidinyl, difluoropyrrolidinyl, fluoro(methyl)pyrrolidinyl. Examples for bicyclic saturated heterocyclyl are azabicyclo[3.2.1]octyl, quinuclidinyl, oxaazabicyclo[3.2.1]octyl, azabicyclo[3.3.1]nonyl, oxaazabicyclo[3.3.1]nonyl, thiaazabicyclo[3.3.1]nonyl, azaspiro[3.3]heptanyl and oxaazaspiro[3.3]heptanyl. Examples for partly unsaturated heterocyclyl are dihydrofuryl, imidazolinyl, dihydrooxazolyl, tetrahydropyridinyl and dihydropyranyl.

The term "enantiomer" denotes two stereoisomers of a compound which are non-superimposable mirror images of one another.

The term "diastereomer" denotes a stereoisomer with two or more centers of chirality and whose molecules are not mirror images of one another. Diastereomers have different physical properties, e.g., melting points, boiling points, spectral properties, and reactivities.

The term "pharmaceutically acceptable salts" denotes salts which are not biologically or otherwise undesirable. Pharmaceutically acceptable salts include both acid and base addition salts.

The term "pharmaceutically acceptable acid addition salt" denotes those pharmaceutically acceptable salts formed with inorganic acids such as hydrochloric acid, hydrobromic acid, sulfuric acid, nitric acid, carbonic acid, phosphoric acid, and organic acids selected from aliphatic, cycloaliphatic, aromatic, araliphatic, heterocyclic, carboxylic, and sulfonic classes of organic acids such as formic acid, acetic acid, propionic acid, glycolic acid, gluconic acid, lactic acid, pyruvic acid, oxalic acid, malic acid, maleic acid, maloneic acid, succinic acid, fumaric acid, tartaric acid, citric acid, aspartic acid, ascorbic acid, glutamic acid, anthranilic acid, benzoic acid, cinnamic acid, mandelic acid, embonic acid, phenylacetic acid, methanesulfonic acid, ethanesulfonic acid, p-toluenesulfonic acid, and salicyclic acid.

The term "pharmaceutically acceptable base addition salt" denotes those pharmaceutically acceptable salts formed with an organic or inorganic base. Examples of acceptable inorganic bases include sodium, potassium, ammonium, calcium, magnesium, iron, zinc, copper, manganese, and aluminum salts. Salts derived from pharmaceutically acceptable organic nontoxic bases includes salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-diethylaminoethanol, trimethamine, dicyclohexylamine, lysine, arginine, histidine, caffeine, procaine, hydrabamine, choline, betaine, ethylenediamine, glucosamine, methylglucamine, theobromine, purines, piperizine, piperidine, N-ethylpiperidine, and polyamine resins.

Compounds of the general formula (I) and their prodrugs which contain one or several chiral centers can either be present as racemates, diastereomeric mixtures, or optically active single isomers. The racemates can be separated according to known methods into the enantiomers. Particularly, diastereomeric salts which can be separated by crystallization are formed from the racemic mixtures by reaction with an optically active acid such as e.g. D- or L-tartaric acid, mandelic acid, malic acid, lactic acid or camphorsulfonic acid.

The term "prodrug" denotes a form or derivative of a compound which is metabolized in vivo, e.g., by biological fluids or enzymes by a subject after administration, into a pharmacologically active form of the compound in order to produce the desired pharmacological effect. Prodrugs are described e.g. in "The Organic Chemistry of Drug Design and Drug Action", by Richard B. Silverman, Academic Press, San Diego, 2004, Chapter 8 Prodrugs and Drug Delivery Systems, pp. 497-558.

"A pharmaceutically active metabolite" is intended to mean a pharmacologically active product produced through metabolism in the body of a specified compound or salt thereof. After entry into the body, most drugs are substrates for chemical reactions that may change their physical properties and biologic effects. These metabolic conversions, which usually affect the polarity of the compounds of the invention, alter the way in which drugs are distributed in and excreted from the body. However, in some cases, metabolism of a drug is required for therapeutic effect.

The term "therapeutically effective amount" denotes an amount of a compound or molecule of the present invention that, when administered to a subject, (i) treats or prevents the particular disease, condition or disorder, (ii) attenuates, ameliorates or eliminates one or more symptoms of the particular disease, condition, or disorder, or (iii) prevents or delays the onset of one or more symptoms of the particular disease, condition or disorder described herein. The therapeutically effective amount will vary depending on the compound, the disease state being treated, the severity of the disease treated, the age and relative health of the subject, the route and form of administration, the judgement of the attending medical or veterinary practitioner, and other factors.

The term "pharmaceutical composition" denotes a mixture or solution comprising a therapeutically effective amount of an active pharmaceutical ingredient together with pharmaceutically acceptable excipients to be administered to a mammal, e.g., a human in need thereof.

TLR7 Agonist and Prodrug

The present invention relates to a compound of formula (I),

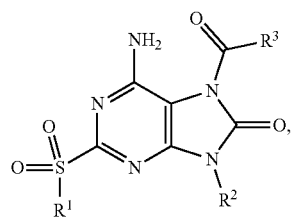

wherein:
$R^1$ is $C_{1-6}$ alkyl;
$R^2$ is phenyl $C_{1-6}$ alkyl, said phenyl being unsubstituted or substituted by one, two or three substituents independently selected from halogen, $C_{1-6}$ alkoxy and $C_{1-6}$ alkyl;
$R^3$ is —$NR^4R^5$, wherein
$R^4$ and $R^5$ are independently selected from $C_{1-6}$ alkyl or $C_{1-6}$ alkoxy $C_{1-6}$ alkyl; or
$R^4$ and $R^5$ together with the nitrogen they are attached to form a heterocyclyl;
or a pharmaceutically acceptable salt, enantiomer or diastereomer thereof.

A further embodiment of present invention is (ii) a compound of formula (I) according to (i), wherein
$R^1$ is $C_{1-6}$ alkyl;
$R^2$ is phenyl $C_{1-6}$ alkyl, said phenyl being unsubstituted or substituted by halogen, $C_{1-6}$ alkoxy or $C_{1-6}$ alkyl;
$R^3$ is pyrrolidinyl or —$NR^4R^5$, wherein
$R^4$ and $R^5$ are independently selected from $C_{1-6}$ alkyl or $C_{1-6}$ alkoxy $C_{1-6}$ alkyl; or a pharmaceutically acceptable salt, enantiomer or diastereomer thereof.

A further embodiment of present invention is (iii) a compound of formula (I) according to (i) or (ii), wherein
$R^1$ is ethyl or propyl;
$R^2$ is benzyl, bromobenzyl, chlorobenzyl, fluorobenzyl, methylbenzyl or methoxybenzyl;
$R^3$ is pyrrolidinyl; or —$NR^4R^5$, wherein $R^4$ and $R^5$ are independently selected from methyl, ethyl, propyl or methoxyethyl.

A further embodiment of present invention is (iv) a compound of formula (I) according to any one of (i) to (iii), wherein $R^3$ is pyrrolidinyl, methyl(ethyl)amino, methyl(propyl)amino, methyl(methoxyethyl)amino or dimethylamino.

A further embodiment of present invention is (v) a compound of formula (I) according to any one of (i) to (iv), wherein $R^2$ is benzyl substituted by halogen or $C_{1-6}$ alkyl.

A further embodiment of present invention is (vi) a compound of formula (I) according to any one of (i) to (v), wherein $R^2$ is bromobenzyl, chlorobenzyl, fluorobenzyl or methylbenzyl.

A further embodiment of present invention is (vii) a compound of formula (I) according to any one of (i) to (vi), wherein $R^2$ is bromobenzyl, chlorobenzyl or fluorobenzyl.

A further embodiment of present invention is (viii) a compound of formula (I) according to any one of (i) to (vii), wherein $R^3$ is —$NR^4R^5$, wherein $R^4$ is $C_{1-6}$ alkyl; $R^5$ is $C_{1-6}$ alkyl.

A further embodiment of present invention is (ix) a compound of formula (I) according to any one of (i) to (viii), $R^3$ is methyl(propyl)amino or methyl(ethyl)amino.

A further embodiment of present invention is (x) a compound of formula (I) according to any one of (i) to (ix), wherein
$R^1$ is $C_{1-6}$ alkyl;
$R^2$ is benzyl, said benzyl being substituted by halogen or $C_{1-6}$ alkyl;
$R^3$ is —$NR^4R^5$, wherein $R^4$ is $C_{1-6}$ alkyl, $R^5$ is $C_{1-6}$ alkyl.

A further embodiment of present invention is (xi) a compound of formula (I) according to any one of (i) to (x), wherein
$R^1$ is ethyl or propyl;
$R^2$ is bromobenzyl, chlorobenzyl or fluorobenzyl;
$R^3$ is methyl(propyl)amino or methyl(ethyl)amino.

Another embodiment of present invention is that (xii) compounds of formula (I) are selected from the following:

6-amino-9-benzyl-N-ethyl-N-methyl-8-oxo-2-propylsulfonyl-purine-7-carboxamide;
6-amino-9-benzyl-N-methyl-8-oxo-N-propyl-2-propylsulfonyl-purine-7-carboxamide;
6-amino-9-benzyl-N-ethyl-2-ethylsulfonyl-N-methyl-8-oxo-purine-7-carboxamide;
6-amino-9-benzyl-2-ethylsulfonyl-N-methyl-8-oxo-N-propyl-purine-7-carboxamide;
6-amino-9-benzyl-2-ethylsulfonyl-7-(pyrrolidine-1-carbonyl)purin-8-one;
6-amino-9-[(4-chlorophenyl)methyl]-N-methyl-8-oxo-N-propyl-2-propylsulfonyl-purine-7-carboxamide;
6-amino-9-[(4-chlorophenyl)methyl]-N-ethyl-N-methyl-8-oxo-2-propylsulfonyl-purine-7-carboxamide;
6-amino-9-[(4-chlorophenyl)methyl]-2-ethylsulfonyl-N-methyl-8-oxo-N-propyl-purine-7-carboxamide;
6-amino-9-[(4-chlorophenyl)methyl]-N-ethyl-2-ethylsulfonyl-N-methyl-8-oxo-purine-7-carboxamide;
6-amino-9-[(4-chlorophenyl)methyl]-2-ethylsulfonyl-N,N-dimethyl-8-oxo-purine-7-carboxamide;
6-amino-9-[(4-chlorophenyl)methyl]-2-ethylsulfonyl-N-(2-methoxyethyl)-N-methyl-8-oxo-purine-7-carboxamide;
6-amino-N-methyl-8-oxo-N-propyl-2-propylsulfonyl-9-(p-tolylmethyl)purine-7-carboxamide;
6-amino-N-ethyl-N-methyl-8-oxo-2-propylsulfonyl-9-(p-tolylmethyl)purine-7-carboxamide;
6-amino-2-ethylsulfonyl-N-methyl-8-oxo-N-propyl-9-(p-tolylmethyl)purine-7-carboxamide;
6-amino-N,N-diethyl-2-ethylsulfonyl-8-oxo-9-(p-tolylmethyl)purine-7-carboxamide;
6-amino-N-ethyl-2-ethylsulfonyl-N-methyl-8-oxo-9-(p-tolylmethyl)purine-7-carboxamide;
6-amino-2-ethylsulfonyl-9-(p-tolylmethyl)-7-(pyrrolidine-1-carbonyl)purin-8-one;
6-amino-2-ethylsulfonyl-9-[(4-fluorophenyl)methyl]-N-methyl-8-oxo-N-propyl-purine-7-carboxamide;
6-amino-N-ethyl-2-ethylsulfonyl-9-[(4-fluorophenyl)methyl]-N-methyl-8-oxo-purine-7-carboxamide;
6-amino-9-[(4-methoxyphenyl)methyl]-N-methyl-8-oxo-N-propyl-2-propylsulfonyl-purine-7-carboxamide;
6-amino-N-ethyl-9-[(4-methoxyphenyl)methyl]-N-methyl-8-oxo-2-propylsulfonyl-purine-7-carboxamide;
6-amino-9-[(4-bromophenyl)methyl]-2-ethylsulfonyl-N-methyl-N-propyl-8-oxo-purine-7-carboxamide; and
6-amino-9-[(4-bromophenyl)methyl]-N-ethyl-2-ethylsulfonyl-N-methyl-8-oxo-purine-7-carboxamide;
or a pharmaceutically acceptable salt, enantiomer or diastereomer thereof.

Synthesis

The compounds of the present invention can be prepared by any conventional means. Suitable processes for synthesizing these compounds as well as their starting materials are provided in the schemes below and in the examples. All substituents, in particular, $R^1$ to $R^{11}$ are as defined above unless otherwise indicated. Furthermore, and unless explicitly otherwise stated, all reactions, reaction conditions, abbreviations and symbols have the meanings well known to a person of ordinary skill in organic chemistry.

Scheme 1

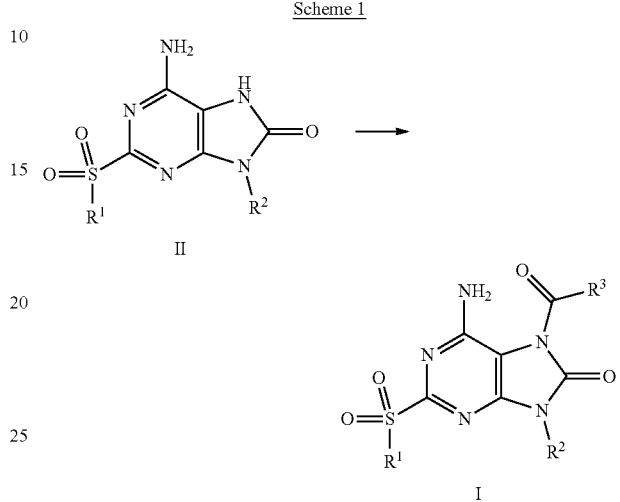

A compound of formula I is obtained by reaction of compound of formula II (synthesis refers to JP1999193282 (JP11193282A)) with carbamoyl chloride in the presence of a mixed base such as pyridine and triethylamine, pyridine and DIPEA, DMAP and triethylamine, or DMAP and DIPEA.

This invention also relates to a process for the preparation of a compound of formula (I) comprising the reaction of:
The reaction of a compound of formula (II),

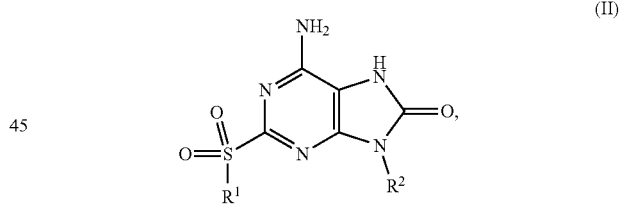

(II)

with carbamoyl chloride in the presence of a mixed base; wherein $R^1$ and $R^2$ are defined above.

In above step, the mixed base can be, for example, pyridine and triethylamine, pyridine and DIPEA, DMAP and triethylamine, or DMAP and DIPEA.

A compound of formula (I) when manufactured according to the above process is also an object of the invention.

Pharmaceutical Compositions and Administration

Another embodiment provides pharmaceutical compositions or medicaments containing the compounds of the invention and a therapeutically inert carrier, diluent or excipient, as well as methods of using the compounds of the invention to prepare such compositions and medicaments. In one example, compounds of formula (I) may be formulated by mixing at ambient temperature at the appropriate pH, and at the desired degree of purity, with physiologically acceptable carriers, i.e., carriers that are non-toxic to recipients at the dosages and concentrations employed into a galenical administration form. The pH of the formulation depends mainly on the particular use and the concentration of compound, but preferably ranges anywhere from about 3 to about 8. In one example, a compound of formula (I) are formulated in an acetate buffer, at pH 5. In another embodiment, the compounds of formula (I) are sterile. The compound may be stored, for example, as a solid or amorphous composition, as a lyophilized formulation or as an aqueous solution.

Compositions are formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The "effective amount" of the compound to be administered will be governed by such considerations, and is the minimum amount necessary to activate TLR7 receptor and lead to produce INF-α and other cytokines, which can be used, but not limited, for the treatment or prevention of hepatitis B and/or C viral infected patients.

In one example, the pharmaceutically effective amount of the compound of the invention administered parenterally per dose will be in the range of about 0.1 to 50 mg/kg, alternatively about 0.1 to 30 mg/kg of patient body weight per day, with the typical initial range of compound used being 0.3 to 15 mg/kg/day. In another embodiment, oral unit dosage forms, such as tablets and capsules, preferably contain from about 20 to about 1000 mg of the compound of the invention.

The compounds of the invention may be administered by any suitable means, including oral, topical (including buccal and sublingual), rectal, vaginal, transdermal, parenteral, subcutaneous, intraperitoneal, intrapulmonary, intradermal, intrathecal and epidural and intranasal, and, if desired for local treatment, intralesional administration. Parenteral infusions include intramuscular, intravenous, intraarterial, intraperitoneal, or subcutaneous administration.

The compounds of the present invention may be administered in any convenient administrative form, e.g., tablets, powders, capsules, solutions, dispersions, suspensions, syrups, sprays, suppositories, gels, emulsions, patches, etc. Such compositions may contain components conventional in pharmaceutical preparations, e.g., diluents, carriers, pH modifiers, sweeteners, bulking agents, and further active agents.

A typical formulation is prepared by mixing a compound of the present invention and a carrier or excipient. Suitable carriers and excipients are well known to those skilled in the art and are described in detail in, e.g., Ansel, Howard C., et al., Ansel's Pharmaceutical Dosage Forms and Drug Delivery Systems. Philadelphia: Lippincott, Williams & Wilkins, 2004; Gennaro, Alfonso R., et al. Remington: The Science and Practice of Pharmacy. Philadelphia: Lippincott, Williams & Wilkins, 2000; and Rowe, Raymond C. Handbook of Pharmaceutical Excipients. Chicago, Pharmaceutical Press, 2005. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents, diluents and other known additives to provide an elegant presentation of the drug (i.e., a compound of the present invention or pharmaceutical composition thereof) or aid in the manufacturing of the pharmaceutical product (i.e., medicament).

An example of a suitable oral dosage form is a tablet containing about 20 to 1000 mg of the compound of the invention compounded with about 30 to 90 mg anhydrous lactose, about 5 to 40 mg sodium croscarmellose, about 5 to 30 mg polyvinylpyrrolidone (PVP) K30, and about 1 to 10 mg magnesium stearate. The powdered ingredients are first mixed together and then mixed with a solution of the PVP. The resulting composition can be dried, granulated, mixed with the magnesium stearate and compressed to tablet form using conventional equipment. An example of an aerosol formulation can be prepared by dissolving the compound, for example 20 to 1000 mg, of the invention in a suitable buffer solution, e.g. a phosphate buffer, adding a tonicifier, e.g. a salt such sodium chloride, if desired. The solution may be filtered, e.g., using a 0.2 micron filter, to remove impurities and contaminants.

An embodiment, therefore, includes a pharmaceutical composition comprising a compound of formula (I) or pharmaceutically acceptable salts or enantiomers or diastereomers thereof.

In a further embodiment includes a pharmaceutical composition comprising a compound of formula (I) or pharmaceutically acceptable salts or enantiomers or diastereomers thereof, together with a pharmaceutically acceptable carrier or excipient.

Another embodiment includes a pharmaceutical composition comprising a compound of formula (I) or pharmaceutically acceptable salts or enantiomers or diastereomers thereof for use in the treatment of hepatitis B virus infection.

Indications and Methods of Treatment

The present invention provides methods for treating or preventing a hepatitis B viral infection and/or hepatitis C viral infection in a patient in need thereof.

The present invention further provides methods for introducing a therapeutically effective amount of a compound of formula (I) or other compounds of the invention into the blood stream of a patient for the treatment and/or prevention of hepatitis B and/or C viral infection.

The methods of the present invention are particularly well suited for human patients. In particular, the methods and doses of the present invention can be useful for, but not limited to, HBV and/or HCV infected patients. The methods and doses of the present invention are also useful for patients undergoing other antiviral treatments. The prevention methods of the present invention are particularly useful for patients at risk of viral infection. These patients include, but are not limited to health care workers, e.g., doctors, nurses, hospice care givers; military personnel; teachers; childcare workers; patients traveling to, or living in, foreign locales, in particular third world locales including social aid workers, missionaries, and foreign diplomats. Finally, the methods and compositions include the treatment of refractory patients or patients resistant to treatment such as resistance to reverse transcriptase inhibitors, protease inhibitors, etc.

Another embodiment includes a method of treating or preventing hepatitis B viral infection and/or hepatitis C viral infection in a mammal in need of such treatment, wherein the method comprises administering to said mammal a therapeutically effective amount of a compound of formula (I) or enantiomers, diastereomers, prodrugs or pharmaceutically acceptable salts thereof.

EXAMPLES

The invention will be more fully understood by reference to the following examples. They should not, however, be construed as limiting the scope of the invention.

ABBREVIATIONS

DCM: dichloromethane
DIEPA: N, N-diethylpropylamine
DMAP: 4-dimethylaminopyridine
$EC_{50}$: the molar concentration of an agonist, which produces 50% of the maximum possible response for that agonist.
EtOAc or EA: ethyl acetate
hr(s): hour(s)
HPLC: high performance liquid chromatography
MS (ESI): mass spectroscopy (electron spray ionization)
obsd. observed
PE: petroleum ether
PMB: p-methoxybenzyl
QOD every other day
QW once a week
RT or rt: room temperature
sat. saturated
TFA: trifluoroacetic acid
TEA: triethylamine
V/V volume ratio
General Experimental Conditions
Intermediates and final compounds were purified by flash chromatography using one of the following instruments: i) Biotage SP1 system and the Quad 12/25 Cartridge module. ii) ISCO combi-flash chromatography instrument. Silica gel Brand and pore size: i) KP-SIL 60 Å, particle size: 40-60 μm; ii) CAS registry NO: Silica Gel: 63231-67-4, particle size: 47-60 micron silica gel; iii) ZCX from Qingdao Haiyang Chemical Co., Ltd, pore: 200-300 or 300-400.

Intermediates and final compounds were purified by preparative HPLC on reversed phase column using X Bridge™ Perp $C_{18}$ (5 μm, OBD™ 30×100 mm) column or SunFire™ Perp $C_{18}$ (5 μm, OBD™ 30×100 mm) column.

LC/MS spectra were obtained using a Waters UPLC-SQD Mass. Standard LC/MS conditions were as follows (running time 3 minutes):

Acidic condition: A: 0.1% formic acid and 1% acetonitrile in $H_2O$; B: 0.1% formic acid in acetonitrile;

Basic condition: A: 0.05% $NH_3 \cdot H_2O$ in $H_2O$; B: acetonitrile.

Mass spectra (MS): generally only ions which indicate the parent mass are reported, and unless otherwise stated the mass ion quoted is the positive mass ion $(M+H)^+$.

NMR Spectra were obtained using Bruker Avance 400 MHz.

All reactions involving air-sensitive reagents were performed under an argon atmosphere. Reagents were used as received from commercial suppliers without further purification unless otherwise noted.

PREPARATIVE EXAMPLES

Example 1

6-Amino-9-benzyl-N-ethyl-N-methyl-8-oxo-2-propylsulfonyl-purine-7-carboxamide

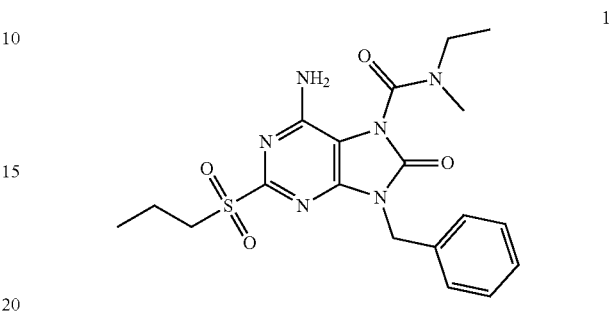

To a solution of 6-amino-9-benzyl-2-propylsulfonyl-7H-purin-8-one (55 mg, 158 μmol, Compound 1a, JP1999193282 (JP11193282A), Page 164, Table 4, Line 5), DMAP (19.3 mg, 158 μmol) and $Et_3N$ (80.1 mg, 110 μL, 792 μmol) in DCM (2 mL) was added N-ethyl-N-methyl-carbamoyl chloride (96.2 mg) at rt. The mixture was stirred at rt for 4 hrs and concentrated in vacuo. The crude material was purified by preparative HPLC to give 6-amino-9-benzyl-N-ethyl-N-methyl-8-oxo-2-propylsulfonyl-purine-7-carboxamide (53 mg, Example 1) as a white solid. $^1$H NMR (400 MHz, DMSO-$d_6$) δ ppm: 7.27-7.38 (m, 5H), 7.06 (br s, 2H), 5.00 (s, 2H), 3.37-3.53 (m, 4H), 3.06 (s, 2H), 3.01 (s, 1H), 1.64 (sxt, J=7.6 Hz, 2H), 1.10-1.25 (m, 3H), 0.94 (t, J=7.5 Hz, 3H). MS obsd. (ESI$^+$) $[(M+H)^+]$: 433.

Example 2

6-Amino-9-benzyl-N-methyl-8-oxo-N-propyl-2-propylsulfonyl-purine-7-carboxamide

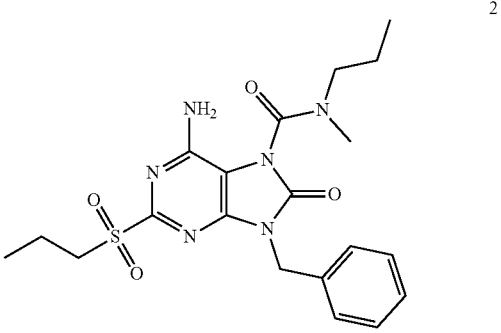 [SMILES: CCCN(C)C(=O)n1c(=O)n(Cc2ccccc2)c2nc(S(=O)(=O)CCC)nc(N)c21]

Example 2 was prepared in analogy to Example 1 by using N-methyl-N-propyl-carbamoyl chloride instead of N-ethyl-N-methyl-carbamoyl chloride. 6-Amino-9-benzyl-N-methyl-8-oxo-N-propyl-2-propylsulfonyl-purine-7-carboxamide (50 mg, Example 2) was obtained as a white solid. $^1$H NMR (400 MHz, DMSO-$d_6$) δ ppm: 7.27-7.40 (m, 5H), 7.04 (br s, 2H), 5.00 (s, 2H), 3.39-3.51 (m, 2H), 3.27-3.35 (m, 2H), 3.06 (s, 2H), 3.03 (m, 1H), 1.54-1.71 (m, 4H), 0.89-0.98 (m, 5H), 0.76 (t, J=7.3 Hz, 1H). MS obsd. (ESI$^+$)$[(M+H)^+]$: 447.

Example 3

6-Amino-9-benzyl-N-ethyl-2-ethylsulfonyl-N-methyl-8-oxo-purine-7-carboxamide

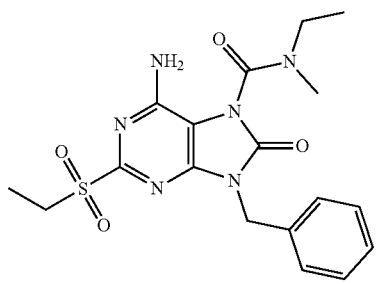

Example 3 was prepared in analogy to Example 1 by using 6-amino-9-benzyl-2-ethylsulfonyl-7H-purin-8-one (Compound 3a, JP1999193282 (JP11193282A), Page 164, Table 4, Line 4) instead of 6-amino-9-benzyl-2-propylsulfonyl-7H-purin-8-one (Compound 1a, JP1999193282 (JP11193282A), Page 164, Table 4, Line 5). 6-Amino-9-benzyl-N-ethyl-2-ethylsulfonyl-N-methyl-8-oxo-purine-7-carboxamide (70 mg, Example 3) was obtained as a white solid. $^1$H NMR (400 MHz, DMSO-d$_6$) δ ppm: 7.27-7.40 (m, 5H), 7.06 (br s, 2H), 5.00 (s, 2H), 3.37-3.56 (m, 4H), 3.06 (s, 2H), 3.01 (s, 1H), 1.14-1.22 (m, 6H). MS obsd. (ESI$^+$) [(M+H)$^+$]: 419.

Example 4

6-Amino-9-benzyl-2-ethylsulfonyl-N-methyl-8-oxo-N-propyl-purine-7-carboxamide

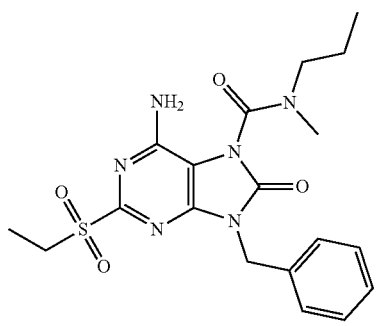

Example 4 was prepared in analogy to Example 1 by using 6-amino-9-benzyl-2-ethylsulfonyl-7H-purin-8-one (Compound 3a, JP1999193282 (JP11193282A), Page 164, Table 4, Line 4) and N-methyl-N-propyl-carbamoyl chloride instead of 6-amino-9-benzyl-2-propylsulfonyl-7H-purin-8-one (Compound 1a, JP1999193282 (JP11193282A), Page 164, Table 4, Line 5) and N-ethyl-N-methyl-carbamoyl chloride. 6-Amino-9-benzyl-2-ethylsulfonyl-N-methyl-8-oxo-N-propyl-purine-7-carboxamide (90 mg, Example 4) was obtained as a white solid. $^1$H NMR (400 MHz, DMSO-d6) δ ppm: 7.27-7.40 (m, 5H), 7.04 (br s, 2H), 5.00 (s, 2H), 3.38-3.55 (m, 2H), 3.27-3.40 (m, 2H), 3.06 (s, 2H), 3.03 (s, 1H), 1.52-1.70 (m, 2H), 1.15-1.24 (m, 3H), 0.91 (t, J=7.3 Hz, 2H), 0.76 (t, J=7.3 Hz, 1H). MS obsd. (ESI$^+$)[(M+H)$^+$]: 433.

Example 5

6-Amino-9-benzyl-2-ethylsulfonyl-7-(pyrrolidine-1-carbonyl)purin-8-one

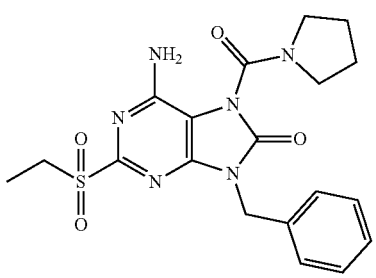

Example 5 was prepared in analogy to Example 1 by using 6-amino-9-benzyl-2-ethylsulfonyl-7H-purin-8-one (Compound 3a, JP1999193282 (JP11193282A), Page 164, Table4, Line4) and pyrrolidine-1-carbonyl chloride instead of 6-amino-9-benzyl-2-propylsulfonyl-7H-purin-8-one (Compound 1a, JP1999193282 (JP11193282A), Page 164, Table 4, Line 5) and N-ethyl-N-methyl-carbamoyl chloride. 6-Amino-9-benzyl-2-ethylsulfonyl-7-(pyrrolidine-1-carbonyl)purin-8-one (21.5 mg, Example 5) was obtained as a white solid. $^1$NMR (400 MHz, DMSO-d$_6$) δ ppm: 7.27-7.39 (m, 5H), 7.01-7.24 (br s, 2H), 5.00 (s, 2H), 3.43-3.64 (m, 6H), 1.81-1.95 (m, 4H), 1.14-1.25 (m, 3H). MS obsd. (ESI$^+$) [(M+H)$^+$]: 431

Example 6

6-Amino-9-[(4-chlorophenyl)methyl]-N-methyl-8-oxo-N-propyl-2-propylsulfonyl-purine-7-carboxamide

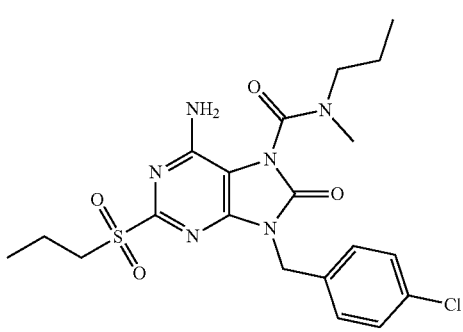

Example 6 was prepared in analogy to Example 1 by using 6-amino-9-[(4-chlorophenyl)methyl]-2-propylsulfonyl-7H-purin-8-one (compound 6a, JP1999193282 (JP11193282A), Page 175, Table 4, Line 4) and N-methyl-N-propyl-carbamoyl chloride instead of 6-amino-9-benzyl-2-propylsulfonyl-7H-purin-8-one (Compound 1a, JP1999193282 (JP11193282A), Page 164, Table 4, Line 5) and N-ethyl-N-methyl-carbamoyl chloride. 6-Amino-9-[(4-chlorophenyl)methyl]-N-methyl-8-oxo-N-propyl-2-propylsulfonyl-purine-7-carboxamide (15 mg, Example 6) was obtained as a white solid. $^1$NMR (400 MHz, DMSO-d$_6$) δ ppm: 7.35-7.46 (m, 4H), 7.04 (br s, 2H), 5.00 (s, 2H), 3.38-3.46 (m, 2H), 3.24-3.35 (m, 2H), 3.06 (s, 2H), 3.02 (s, 1H), 1.52-1.69 (m, 4H), 0.88-0.96 (m, 5H), 0.76 (t, J=8.0 Hz, 1H). MS obsd. (ESI⁺) [(M+H)⁺]: 481.

Example 7

6-Amino-9-[(4-chlorophenyl)methyl]-N-ethyl-N-methyl-8-oxo-2-propylsulfonyl-purine-7-carboxamide

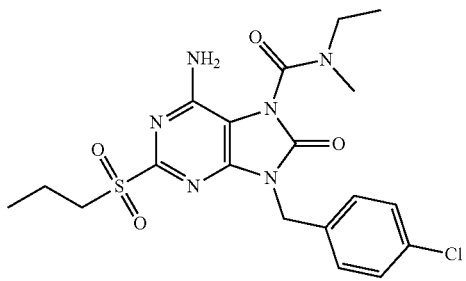

7

Example 7 was prepared in analogy to Example 1 by using 6-amino-9-[(4-chlorophenyl)methyl]-2-propylsulfonyl-7H-purin-8-one (Compound 6a, JP1999193282 (JP11193282A), Page 175, Table 4, Line 4) instead of 6-amino-9-benzyl-2-propylsulfonyl-7H-purin-8-one (Compound 1a, JP1999193282 (JP11193282A), Page 164, Table 4, Line 5). 6-Amino-9-[(4-chlorophenyl)methyl]-N-ethyl-N-methyl-8-oxo-2-propylsulfonyl-purine-7-carboxamide (187 mg, Example 7) was obtained as a white solid. $^1$NMR (400 MHz, DMSO-d$_6$) δ ppm: 7.36-7.45 (m, 4H), 7.07 (br s, 2H), 4.99 (s, 2H), 3.38-3.47 (m, 2H), 3.27-3.35 (m, 2H), 3.06 (s, 2H), 3.01 (m, 1H), 1.62 (sxt, J=7.6 Hz, 2H), 1.09-1.25 (m, 3H), 0.93 (t, J=7.5 Hz, 3H). MS obsd. (ESI⁺) [(M+H)⁺]: 467.

Example 8

6-Amino-9-[(4-chlorophenyl)methyl]-2-ethylsulfonyl-N-methyl-8-oxo-N-propyl-purine-7-carboxamide

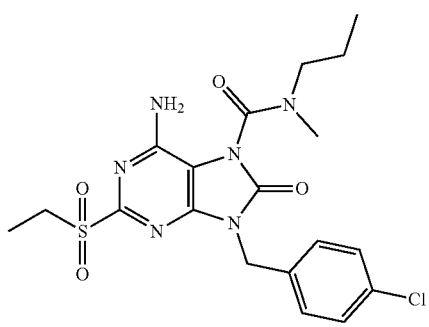

8

Example 8 was prepared in analogy to Example 1 by using 6-amino-9-[(4-chlorophenyl)methyl]-2-ethylsulfonyl-7H-purin-8-one (Compound 8a, JP1999193282 (JP11193282A), Page 173, Table 4, Line 4) and N-methyl-N-propyl-carbamoyl chloride instead of 6-amino-9-benzyl-2-propyl sulfonyl-7H-purin-8-one (Compound 1a, JP1999193282 (JP11193282A), Page 164, Table 4, Line 5) and N-ethyl-N-methyl-carbamoyl chloride. 6-Amino-9-[(4-chlorophenyl)methyl]-2-ethylsulfonyl-N-methyl-8-oxo-N-propyl-purine-7-carboxamide (164 mg, Example 8) was obtained as a white solid. $^1$NMR (400 MHz, DMSO-d$_6$) δ ppm: 7.49-7.32 (m, 4 H), 7.25-6.91 (m, 2 H), 5.00 (s, 2 H), 3.47 (q, J=7.28 Hz, 2 H), 3.33 (s, 2 H), 3.11-3.00 (m, 3 H), 1.71-1.51 (m, 2 H), 1.25-1.14 (m, 3 H), 0.97-0.70 (m, 3 H). MS obsd. (ESI⁺) [(M+H)⁺]: 467.

Example 9

6-Amino-9-[(4-chlorophenyl)methyl]-N-ethyl-2-ethylsulfonyl-N-methyl-8-oxo-purine-7-carboxamide

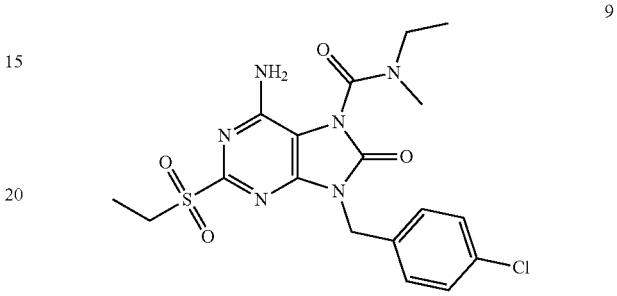

9

Example 9 was prepared in analogy to Example 1 by using 6-amino-9-(4-chlorobenzyl)-2-ethylsulfonyl-7H-purin-8-one (Compound 8a, JP1999193282 (JP11193282A), Page 173, Table 4, Line4) instead of 6-amino-9-benzyl-2-propylsulfonyl-7H-purin-8-one (Compound 1a, JP1999193282 (JP11193282A), Page 164, Table 4, Line 5). 6-Amino-9-[(4-chlorophenyl)methyl]-N-ethyl-2-ethylsulfonyl-N-methyl-8-oxo-purine-7-carboxamide (60 mg, Example 9) was obtained as a white solid. $^1$NMR (400 MHz, DMSO-d$_6$) δ ppm: 7.36-7.45 (m, 4H), 7.07 (br s, 2H), 4.99 (s, 2H), 3.37-3.55 (m, 2H), 3.30-3.37 (m, 2H), 3.05 (s, 2H), 3.01 (s, 1H), 1.11-1.24 (m, 6H). MS obsd. (ESI⁺) [(M+H)⁺]: 453.

Example 10

6-Amino-9-[(4-chlorophenyl)methyl]-2-ethylsulfonyl-N,N-dimethyl-8-oxo-purine-7-carboxamide

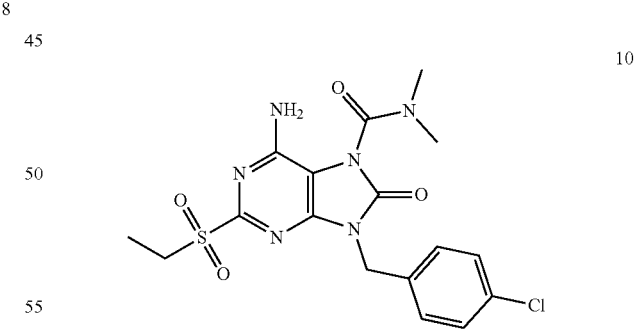

10

Example 10 was prepared in analogy to Example 1 by using 6-Amino-9-(4-chlorobenzyl)-2-ethylsulfonyl-7H-purin-8-one (Compound 8a, JP1999193282 (JP11193282A), Page 173, Table 4, Line4) and N, N-dimethylcarbamoyl chloride instead of 6-amino-9-benzyl-2-propyl sulfonyl-7H-purin-8-one (Compound 1a, JP1999193282 (JP11193282A), Page 164, Table 4, Line 5) and N-ethyl-N-methyl-carbamoyl chloride. 6-Amino-9-[(4-chlorophenyl)methyl]-2-ethylsulfonyl-N,N-dimethyl-8-oxo-purine-7-carboxamide (37 mg, Example 10) was obtained as a white solid. $^1$H NMR (400 MHz, DMSO-d$_6$) δ ppm: 7.37-7.40 (m, 4H), 7.14 (br s, 2H), 4.99 (s, 2H), 3.37-3.55 (m, 2H), 3.06 (s, 3H), 3.03 (s, 3H), 1.18 (t, J=7.4 Hz, 3H). MS obsd. (ESI$^+$) [(M+H)$^+$]: 439.

Example 11

6-Amino-9-[(4-chlorophenyl)methyl]-2-ethylsulfonyl-N-(2-methoxyethyl)-N-methyl-8-oxo-purine-7-carboxamide

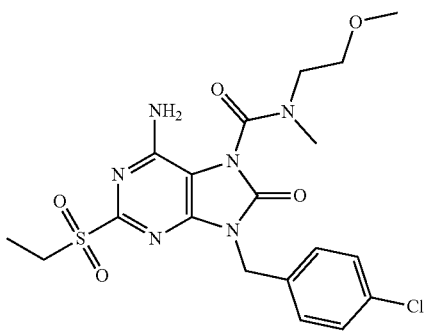

Example 11 was prepared in analogy to Example 1 by using 6-amino-9-(4-chlorobenzyl)-2-ethylsulfonyl-7H-purin-8-one (compound 8a, JP1999193282 (JP11193282A), Page 173, Table 4, Line 4) and N-(2-methoxyethyl)-N-methyl-carbamoyl chloride instead of 6-amino-9-benzyl-2-propylsulfonyl-7H-purin-8-one (Compound 1a, JP1999193282 (JP11193282A), Page 164, Table 4, Line 5) and N-ethyl-N-methyl-carbamoyl chloride. 6-Amino-9-[(4-chlorophenyl)methyl]-2-ethylsulfonyl-N-(2-methoxyethyl)-N-methyl-8-oxo-purine-7-carboxamide (25 mg, Example 11) was obtained as a white solid. $^1$H NMR (400 MHz, DMSO-d$_6$) δ ppm: 7.36-7.45 (m, 4H), 7.06 (br s, 2H), 4.99 (s, 2H), 3.57-3.68 (m, 2H), 3.43-3.51 (m, 2H), 3.31-3.37 (m, 2H), 3.29 (s, 2H), 3.14 (s, 1H), 3.10 (s, 2H), 3.05 (s, 1H), 1.18 (t, J=8.0 Hz, 3H). MS obsd. (ESI$^+$) [(M+H)$^+$]: 483

Example 12

6-Amino-N-methyl-8-oxo-N-propyl-2-propylsulfonyl-9-(p-tolylmethyl)purine-7-carboxamide

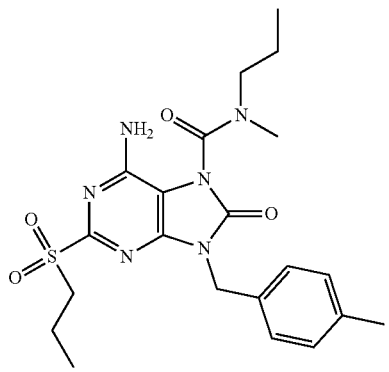

Preparation of 6-amino-2-(propylsulfonyl)-9-(p-tolylmethyl)-7H-purin-8-one (Compound 12a)

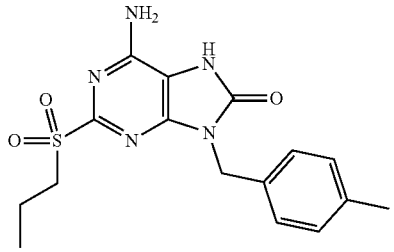

Compound 12a was prepared according to the method disclosed in JP1999193282 (JP11193282A). 6-Amino-2-(propylsulfonyl)-9-(p-tolylmethyl)-7H-purin-8-one (127 mg, Compound 12a) was obtained as a white solid. $^1$H NMR (400 MHz, DMSO-d6) δ ppm: 10.67 (br. s., 1H), 7.23 (d, J=8.0 Hz, 2H), 7.13 (d, J=8.0 Hz, 2H), 6.98 (br. s., 2H), 4.91 (s, 2H), 3.34-3.27 (m, 2H), 2.26 (s, 3H), 1.67-1.62 (m, 2H), 0.92 (t, J=8.0 Hz, 3H). MS obsd. (ESI$^+$) [(M+H)$^+$]: 362.

Preparation of 6-amino-2-propylsulfonyl-N-methyl-8-oxo-N-propyl-9-(p-tolylmethyl)purine-7-carboxamide

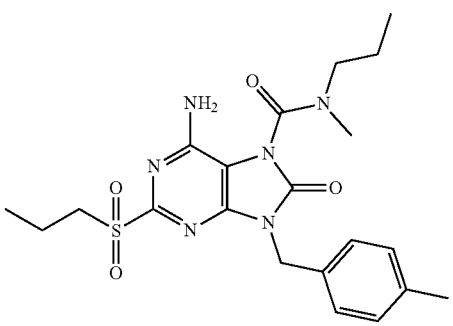

Example 12 was prepared in analogy to Example 1 by using 6-amino-2-propylsulfonyl-9-(p-tolylmethyl)-7H-purin-8-one (compound 12a) and N-methyl-N-propyl-carbamoyl chloride instead of 6-amino-9-benzyl-2-propyl sulfonyl-7H-purin-8-one (Compound 1a, JP1999193282 (JP11193282A), Page 164, Table 4, Line 5) and N-methyl-N-ethyl-carbamoyl chloride. 6-Amino-2-ethylsulfonyl-N-methyl-8-oxo-N-propyl-9-(p-tolylmethyl)purine-7-carboxamide (37 mg, Example 12) was obtained as a white solid. $^1$H NMR (400 MHz, DMSO-d$_6$) δ ppm: 7.19-7.31 (m, 2H), 7.15 (d, J=7.58 Hz, 2H), 7.03 (br s, 2H), 4.95 (s, 2H), 3.35-3.62 (m, 4H), 3.01-3.08 (m, 3H), 2.26 (s, 3H), 1.44-1.75 (m, 4H), 0.60-1.06 (m, 6H). MS obsd. (ESI$^+$) [(M+H)$^+$]: 461.

Example 13

6-Amino-N-ethyl-N-methyl-8-oxo-2-propylsulfonyl-9-(p-tolylmethyl)purine-7-carboxamide

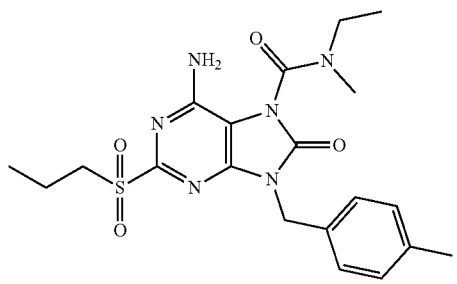

13

Example 13 was prepared in analogy to Example 1 by using 6-amino-2-propylsulfonyl-9-(p-tolylmethyl)-7H-purin-8-one (compound 12a) instead of 6-amino-9-benzyl-2-propylsulfonyl-7H-purin-8-one (Compound 1a, JP1999193282 (JP11193282A), Page 164, Table 4, Line 5). 6-Amino-N-ethyl-N-methyl-8-oxo-2-propylsulfonyl-9-(p-tolylmethyl)purine-7-carboxamide (50 mg, Example 13) was obtained as a white solid. $^1$H NMR (400 MHz, DMSO-d6) δ ppm: 7.25 (d, J=7.95 Hz, 2H), 7.14 (d, J=7.95 Hz, 2H), 6.94-7.09 (m, 2H), 4.94 (s, 2H), 3.36-3.54 (m, 4H), 3.00-3.08 (m, 3H), 2.26 (s, 3H), 1.64 (sxt, J=7.58 Hz, 2H), 1.11-1.23 (m, 3H), 0.95 (t, J=7.46 Hz, 3H). MS obsd. (ESI$^+$) [(M+H)$^+$]: 447

Example 14

6-Amino-2-ethylsulfonyl-N-methyl-8-oxo-N-propyl-9-(p-tolylmethyl)purine-7-carboxamide

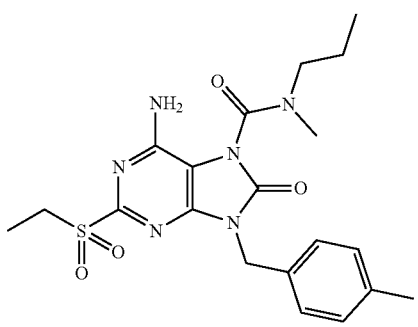

14

Preparation of 6-amino-2-ethylsulfonyl-9-(p-tolylmethyl)-7H-purin-8-one (Compound 14a)

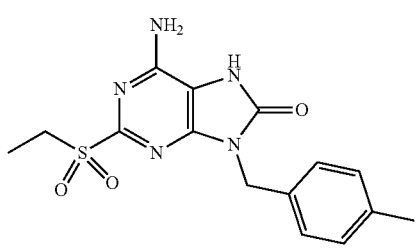

14a

Compound 14a was prepared according to the method disclosed in JP1999193282 (JP11193282A). 6-Amino-2-ethylsulfonyl-9-(p-tolylmethyl)-7H-purin-8-one (37 mg, Compound 14a) was obtained as a yellow solid. MS obsd. (ESI$^+$) [(M+H)$^{30}$]: 348

Preparation 6-amino-2-ethylsulfonyl-N-methyl-8-oxo-N-propyl-9-(p-tolylmethyl)purine-7-carboxamide

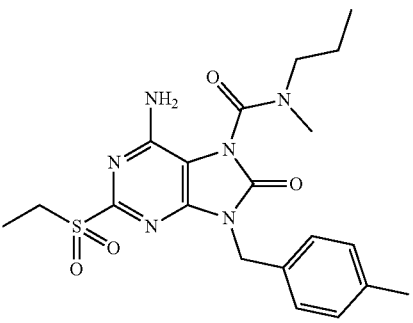

14

Example 14 was prepared in analogy to Example 1 by using 6-amino-2-ethylsulfonyl-9-(p-tolylmethyl)-7H-purin-8-one (3.5 g, Compound 14a) and N-methyl-N-propyl-carbamoyl chloride instead of 6-amino-9-benzyl-2-propylsulfonyl-7H-purin-8-one (Compound 1a, JP1999193282 (JP11193282A), Page 164, Table 4, Line 5) and N-ethyl-N-methyl-carbamoyl chloride. 6-Amino-2-ethylsulfonyl-N-methyl-8-oxo-N-propyl-9-(p-tolylmethyl)purine-7-carboxamide (87.9 mg, Example 14) was obtained as a white solid. $^1$H NMR (400 MHz, DMSO-d6) δ ppm: 7.26 (t, J=12 Hz, 2H), 7.15 (d, J=7.6 Hz, 2H), 7.04 (br s, 2H), 4.95 (s, 2H), 3.46-3.51 (m, 4H), 3.05 (s, 3H), 2.27 (s, 3H), 1.62-1.64 (m, 2H), 1.18-1.23 (m, 3H), 0.74-0.93 (m,3H). MS obsd. (ESI$^+$) [(M+H)$^{30}$]: 447.

Example 15

6-Amino-N,N-diethyl-2-ethylsulfonyl-8-oxo-9-(p-tolylmethyl)purine-7-carboxamide

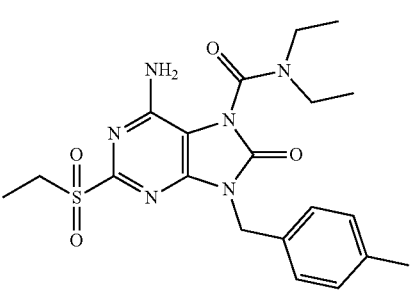

15

Example 15 was prepared in analogy to Example 1 by using 6-amino-2-ethylsulfonyl-9-(p-tolylmethyl)-7H-purin-8-one (Compound 14a) and N, N-diethylcarbamoyl chloride instead of 6-amino-9-benzyl-2-propylsulfonyl-7H-purin-8-one (Compound 1a, JP1999193282 (JP11193282A), Page 164, Table 4, Line 5) and N-ethyl-N-methyl-carbamoyl chloride. 6-Amino-N,N-diethyl-2-ethylsulfonyl-8-oxo-9-(p-tolylmethyl)purine-7-carboxamide (111 mg, Example 15) was obtained as a white solid. $^1$H NMR (400 MHz, DMSO-d$_6$) δ ppm: 7.25 (m, J=7.95 Hz, 2H), 7.15 (d, J=7.95 Hz, 2H), 6.99 (br s, 2H), 4.94 (s, 2H), 3.34-3.58 (m, 6H), 2.26 (s, 3H), 1.10-1.24 (m, 9H). MS obsd. (ESI$^+$) [(M+H)$^{30}$]: 447.

Example 16

6-Amino-N-ethyl-2-ethylsulfonyl-N-methyl-8-oxo-9-(p-tolylmethyl)purine-7-carboxamide

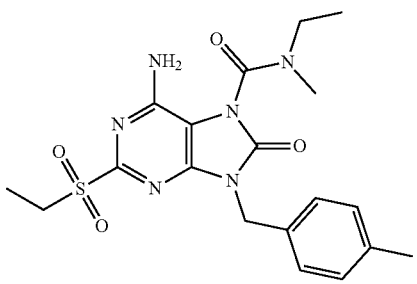

16

Example 16 was prepared in analogy to Example 1 by using 6-amino-2-ethylsulfonyl-9-(p-tolylmethyl)-7H-purin-8-one (Compound 14a) instead of 6-amino-9-benzyl-2-propylsulfonyl-7H-purin-8-one (Compound 1a, JP1999193282 (JP11193282A), Page 164, Table 4, Line 5). 6-Amino-N-ethyl-2-ethylsulfonyl-N-methyl-8-oxo-9-(p-tolylmethyl)purine-7-carboxamide (17 mg, Example 16) was obtained as a white solid. $^1$H NMR (400 MHz, DMSO-d$_6$) δ ppm: 7.25 (d, J=7.9 Hz, 2H), 7.15 (d, J=7.9 Hz, 2H), 7.05 (br s, 2H), 4.94 (s, 2H), 3.37-3.56 (m, 2H), 3.27-3.35 (m, 2H), 3.05 (s, 2H), 3.01 (s, 1H), 2.26 (s, 3H), 1.12-1.24 (m, 6H). MS obsd. (ESI$^+$) [(M+H)$^{30}$]: 433.

Example 17

6-Amino-2-ethylsulfonyl-9-(p-tolylmethyl)-7-(pyrrolidine-1-carbonyl)purin-8-one

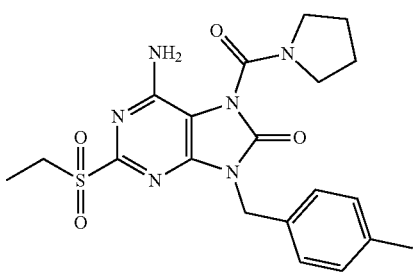

17

Example 17 was prepared in analogy to Example 1, method A, Step 5 by using 6-amino-2-ethylsulfonyl-9-(p-tolylmethyl)-7H-purin-8-one (Compound 14a) and pyrrolidine-1-carbonyl chloride instead of 6-amino-9-benzyl-2-propylsulfonyl-7H-purin-8-one (Compound 1a, JP1999193282 (JP11193282A), Page 164, Table 4, Line 5) and N-ethyl-N-methyl-carbamoyl chloride. 6-Amino-2-ethylsulfonyl-9-(p-tolylmethyl)-7-(pyrrolidine-1-carbonyl)purin-8-one (63 mg, Example 17) was obtained as a white solid. $^1$H NMR (400 MHz, DMSO-d6) δ ppm: 7.25 (d, J=8.07 Hz, 2H), 7.11-7.20 (m, 2H), 4.95 (s, 2H), 3.37-3.63 (m, 6H), 2.26 (s, 3H), 1.81-1.95 (m, 4H), 1.19 (t, J=7.34 Hz, 3 H). MS obsd. (ESI$^+$) [(M+H)$^{30}$]: 445.

Example 18

6-Amino-2-ethylsulfonyl-9-[(4-fluorophenyl)methyl]-N-methyl-8-oxo-N-propyl-purine-7-carboxamide

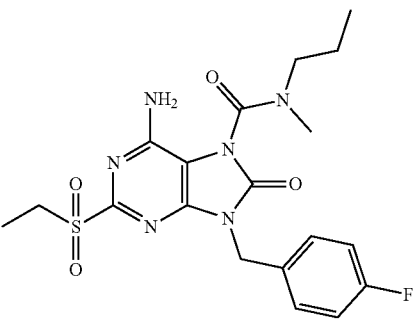

18

Example 18 was prepared in analogy to Example 1 by using 6-Amino-2-ethylsulfonyl-9-[(4-fluorophenyl)methyl]-7H-purin-8-one (compound 18a, JP1999193282 (JP11193282A), Page 173, Table 4, Line 7) and N-methyl-N-propyl-carbamoyl chloride instead of 6-amino-9-benzyl-2-propylsulfonyl-7H-purin-8-one (Compound 1a, JP1999193282 (JP11193282A), Page 164, Table 4, Line 5) and N-ethyl-N-methyl-carbamoyl chloride. 6-Amino-2-ethylsulfonyl-9-[(4-fluorophenyl)methyl]-N-methyl-8-oxo-N-propyl-purine-7carboxamide (95.7 mg, Example 18) was obtained as a white solid. $^1$H NMR (400 MHz, DMSO-d$_6$) δ ppm: 7.32-7.52 (m, 2H), 7.13-7.26 (m, 2H), 6.83-7.13 (m, 2H), 4.88-5.11 (m, 2H), 3.42-3.55 (m, 2H),3.28-3.35 (m, 2H), 3.00-3.08 (m, 3H), 0.91 (s, 3H), 1.49-1.71 (m, 2H), 1.19 (s, 3H). MS obsd. (ESI$^+$) [(M+H)$^{30}$]: 451.

Example 19

6-Amino-N-ethyl-2-ethylsulfonyl-9-[(4-fluorophenyl)methyl]-N-methyl-8-oxo-purine-7-carboxamide

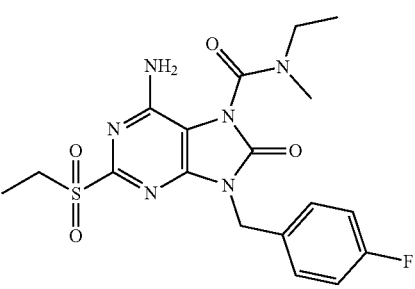

19

Example 19 was prepared in analogy to Example 1 by using 6-amino-2-ethylsulfonyl-9-[(4-fluorophenyl)methyl]-7H-purin-8-one (compound 18a, JP1999193282 (JP11193282A), Page 173, Table 4, Line 7) instead of 6-amino-9-benzyl-2-propylsulfonyl-7H-purin-8-one (compound 1a, JP1999193282 (JP11193282A), Page 164, Table 4, Line 5). 6-Amino-N-ethyl-2-ethylsulfonyl-9-[(4-fluorophenyl)methyl]-N-methyl-8-oxo-purine-7-carboxamide (59 mg, Example 19) was obtained as a white solid. $^1$H NMR (400 MHz, DMSO-d$_6$) δ ppm: 7.38-7.46 (m, 2H), 7.10-7.24

(m, 2H), 6.89-7.10 (m, 2H), 4.98 (s, 2H), 3.37-3.56 (m, 4H), 3.00-3.08 (m, 3H), 1.14-1.23 (m, 6H). MS obsd. (ESI+) [(M+H)$^{3O}$]: 437.

Example 20

6-Amino-9-[(4-methoxyphenyl)methyl]-N-methyl-8-oxo-N-propyl-2-propylsulfonyl-purine-7-carboxamide

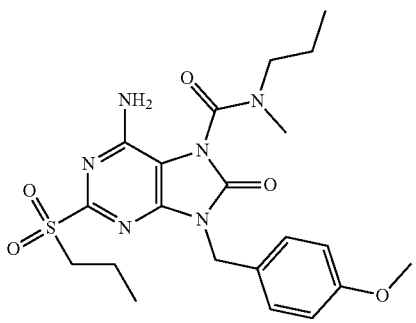

Example 20 was prepared in analogy to Example 1, method A, Step 5 by using 6-Amino-2-ethylsulfonyl-9-[(4-fluorophenyl)methyl]-7H-purin-8-one (compound 20a, JP1999193282 (JP11193282A), Page 175, Table 4, Line 16) instead of 6-amino-9-benzyl-2-propylsulfonyl-7H-purin-8-one (compound 1a, JP1999193282 (JP11193282A), Page 164, Table 4, Line 5) and N-ethyl-N-methyl-carbamoyl chloride. 6-Amino-9-[(4-methoxyphenyl)methyl]-N-methyl-8-oxo-N-propyl-2-propylsulfonyl-purine-7-carboxamide (28 mg, Example 20) was obtained as a white solid. $^1$H NMR (400 MHz, DMSO-d$_6$) δ ppm: 7.28-7.35 (m, 2H), 7.03 (br s, 2H), 6.87-6.93 (m, 2H), 4.92 (s, 2H), 3.71 (s, 3H), 3.38-3.49 (m, 2H), 3.27-3.38 (m, 2H), 3.05 (s, 2H), 3.02 (s, 1H), 1.53-1.71 (m, 4H), 0.89-0.99 (m, 5H), 0.75 (t, J=7.3 Hz, 1H). MS obsd. (ESI+) [(M+H)$^{3O}$]: 477.

Example 21

6-Amino-N-ethyl-9-[-(4-methoxyphenyl)methyl]-N-methyl-8-oxo-2-propylsulfonyl-purine-7-carboxamide

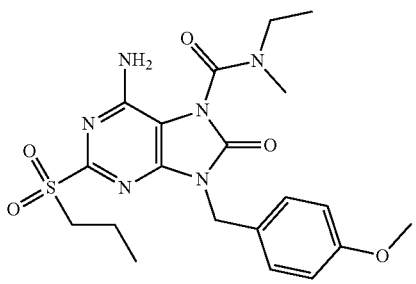

Example 21 was prepared in analogy to Example 1 by using 6-Amino-2-ethylsulfonyl-9-[(4-fluorophenyl)methyl]-7H-purin-8-one (compound 20a, JP1999193282 (JP11193282A), Page 175, Table 4, Line 16) instead of 6-amino-9-benzyl-2-propylsulfonyl-7H-purin-8-one (Compound 1a, JP1999193282 (JP11193282A), Page 164, Table 4, Line 5). 6-Amino-N-ethyl-9-[(4-methoxyphenyl)methyl]-N-methyl-8-oxo-2-propylsulfonyl-purine-7-carboxamide (64 mg, Example 21) was obtained as a white solid. $^1$H NMR (400 MHz, DMSO-d$_6$) δ ppm: 7.27-7.34 (m, 2H), 7.04 (br s, 2H), 6.87-6.93 (m, 2H), 4.92 (s, 2H), 3.71 (s, 3H), 3.35-3.50 (m, 2H), 3.29-3.34 (m, 2H), 3.05 (s, 2H), 3.01 (m, 1H), 1.66 (sxt, J=7.6 Hz, 2H), 1.11-1.23 (m, 3H), 0.96 (t, J=7.5 Hz, 3H). MS obsd. (ESI+) [(M+H)$^{3O}$]: 463.

Example 22

6-Amino-9-[(4-bromophenyl)methyl]-2-ethylsulfonyl-N-methyl-N-propyl-8-oxo-purine-7-carboxamide

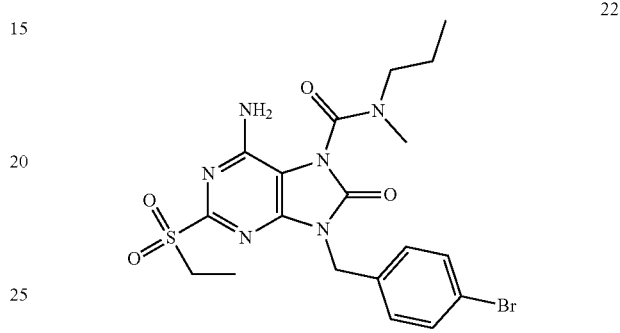

Example 22 was prepared in analogy to Example 1 by using 6-Amino-2-ethylsulfonyl-9-[(4-bromophenyl)methyl]-7H-purin-8-one (compound 22a, JP1999193282 (JP11193282A), Page 173, Table 4, Line 10) and N-methyl-N-propyl-carbamoyl chloride instead of 6-amino-9-benzyl-2-propylsulfonyl-7H-purin-8-one (Compound 1a, JP1999193282 (JP11193282A), Page 164, Table 4, Line 5) and N-ethyl-N-methyl-carbamoyl chloride.

6-Amino-9-[(4-bromophenyl)methyl]-2-ethylsulfonyl-N-methyl-N-propyl-8-oxo-purine-7-carboxamide (18 mg, Example 22) was obtained as a white solid. $^1$H NMR (400 MHz, DMSO-d6) δ ppm: 7.49-7.60 (m, 2H), 7.33 (br d, J=8.44 Hz, 2H), 7.05 (br s, 2H), 4.97 (s, 2H), 3.35-3.54 (m, 2H), 3.28-3.33 (m, 2H), 3.01-3.09 (m, 3H), 1.52-1.69 (m, 2H), 1.14-1.23 (m, 3H), 0.67-0.99 (m, 3H). MS obsd. (ESI+) [(M+H)$^{3O}$]: 511

Example 23

6-Amino-9-[(4-bromophenyl)methyl]-N-ethyl-2-ethylsulfonyl-N-methyl-8-oxo-purine-7-carboxamide

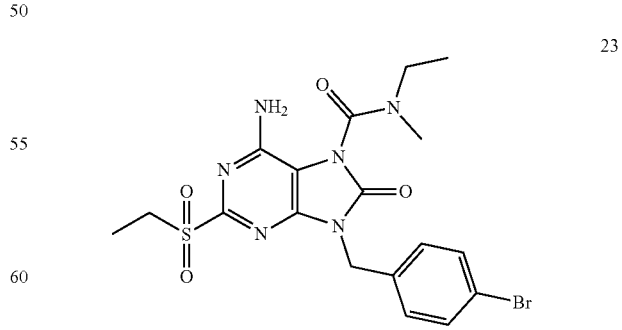

Example 23 was prepared in analogy to Example 1 by using 6-Amino-2-ethylsulfonyl-9-[(4-bromophenyl)methyl]-7H-purin-8-one (Compound 22a, JP1999193282 (JP11193282A), Page 173, Table 4, Line 10) instead of 6-amino-9-benzyl-2-propylsulfonyl-7H-purin-8-one (Compound 1a, JP1999193282 (JP11193282A), Page 164, Table 4, Line 5). 6-Amino-N-ethyl-9-[(4-bromophenyl)methyl]-N-methyl-8-oxo-2-ethylsulfonyl-purine-7-carboxamide (11.5 mg, Example 23) was obtained as a white solid. $^1$H NMR (400 MHz, DMSO-d$_6$) δ ppm: 7.55 (d, J=8.44 Hz, 2H), 7.33 (br d, J=8.31 Hz, 2H), 7.08 (br s, 2H), 4.97 (s, 2H), 3.37-3.54 (m, 4H), 2.99-3.08 (m, 3H), 1.12-1.23 (m, 6H). MS obsd. (ESI$^+$) [(M+H)$^{30}$]: 497.

Example 24

Activity of Compounds and Examples in HEK293-hTLR-7 Assay

HEK293-Blue-hTLR-7 Cells Assay

A stable HEK293-Blue-hTLR-7 cell line was purchased from InvivoGen (Cat. #: hkb-htlr7, San Diego, Calif., USA). These cells were designed for studying the stimulation of human TLR7 by monitoring the activation of NF-κB. A SEAP (secreted embryonic alkaline phosphatase) reporter gene was placed under the control of the IFN-β minimal promoter fused to five NF-κB and AP-1-binding sites. The SEAP was induced by activating NF-κB and AP-1 via stimulating HEK-Blue hTLR7 cells with TLR7 ligands. Therefore the reporter expression was regulated by the NF-κB promoter upon stimulation of human TLR7 for 20 hrs. The cell culture supernatant SEAP reporter activity was determined using QUANTI-Blue™ kit (Cat. #: rep-qb1, Invivogen, San Diego, Calif., USA) at a wavelength of 640 nm, a detection medium that turns purple or blue in the presence of alkaline phosphatase.

HEK293-Blue-hTLR7 cells were incubated at a density of 250,000~450,000 cells/mL in a volume of 180 μL in a 96-well plate in Dulbecco's Modified Eagle's medium (DMEM) containing 4.5 g/L glucose, 50 U/mL penicillin, 50 mg/mL streptomycin, 100 mg/mL Normocin, 2 mM L-glutamine, 10% (V/V) heat-inactivated fetal bovine serum for 24 hrs. Then the HEK293-Blue-hTLR-7 cells were incubated with addition of 20 μL test compound in a serial dilution in the presence of final DMSO at 1% and perform incubation under 37° C. in a CO$_2$ incubator for 20 hrs. Then 20 μL of the supernatant from each well was incubated with 180 μL Quanti-blue substrate solution at 37° C. for 2 hrs and the absorbance was read at 620~655 nm using a spectrophotometer. The signalling pathway that TLR7 activation leads to downstream NF-κB activation has been widely accepted, and therefore similar reporter assay was also widely used for evaluating TLR7 agonist (Tsuneyasu Kaisho and Takashi Tanaka, Trends in Immunology, Volume 29, Issue 7, July 2008, Pages 329.sci; Hiroaki Hemmi et al, Nature Immunology 3, 196-200 (2002)).

The Compounds and Examples of the present invention were tested in HEK293-hTLR-7 assay for their TLR7 agonism activity as described herein and results are listed in Table 1. The Examples of prodrugs were found to have EC$_{50}$ of about 2.3 μM to about 494 μM, the Compounds of active forms were found to have EC$_{50}$ less than 0.1 μM. The calculated ratio of EC$_{50(prodrug)}$/EC$_{50(active\ form)}$ were within the range from 27.7 to about 8233.

TABLE 1

Activity of Examples and Compounds of present invention in HEK293-hTLR-7 assay

| Prodrug | HEK293-hTLR-7 EC$_{50}$ (Prodrug, μM) | Corresponding Active Form | HEK293-hTLR-7 EC$_{50}$ (Active form, μM) | Ratio (EC$_{50(prodrug)}$/EC$_{50(active\ form)}$) |
|---|---|---|---|---|
| Example 1 | 10.9 | Compound 1a | 0.075 | 145.3 |
| Example 2 | 6.5 | Compound 1a | 0.075 | 86.7 |
| Example 3 | 104.4 | Compound 3a | 0.17 | 614.1 |
| Example 4 | 87.5 | Compound 3a | 0.17 | 514.7 |
| Example 5 | 29.7 | Compound 3a | 0.17 | 174.7 |
| Example 6 | 2.6 | Compound 6a | 0.021 | 123.8 |
| Example 7 | 3.2 | Compound 6a | 0.021 | 152.4 |
| Example 8 | 14.9 | Compound 8a | 0.083 | 179.5 |
| Example 9 | 18.2 | Compound 8a | 0.083 | 219.3 |
| Example 10 | 2.3 | Compound 8a | 0.083 | 27.7 |
| Example 11 | 10.1 | Compound 8a | 0.083 | 121.7 |
| Example 12 | 3.3 | Compound 12a | 0.065 | 50.8 |
| Example 13 | 9.6 | Compound 12a | 0.065 | 147.7 |
| Example 14 | 68.5 | Compound 14a | 0.065 | 1053 |
| Example 15 | 5.6 | Compound 14a | 0.065 | 86.2 |
| Example 16 | 43.9 | Compound 14a | 0.065 | 445.9 |
| Example 17 | 67 | Compound 14a | 0.065 | 1030.8 |
| Example 18 | 2.4 | Compound 18a | 0.06 | 40 |
| Example 19 | 494 | Compound 18a | 0.06 | 8233 |
| Example 20 | 32.1 | Compound 20a | 0.008 | 4012.5 |
| Example 21 | 24.2 | Compound 20a | 0.008 | 3025 |
| Example 22 | 13.1 | Compound 22a | 0.023 | 570 |
| Example 23 | >100 | Compound 22a | 0.023 | >4348 |

Example 25

Metabolism of Prodrugs of Compound of Formula (I)

A study was undertaken to evaluate the metabolic conversion of prodrugs, compound of formula (I), to its corresponding active form. The compounds of formula (I), if served as prodrugs, can be metabolized to the active compound or other compounds of the invention in the body. Human liver microsomes are often used to assess the degree of metabolic conversion of prodrugs in the body of animal or human.

Materials

NADPH cofactor system including β-Nicotinamide adenine dinucleotide phosphate (NADP), isocitric acid and isocitric dehydrogenase were purchased from Sigma-Aldrich Co. (St. Louis, Mo., USA). Human liver microsomes (Cat No. 452117, Lot No. 38290) were obtained from Corning (Woburn, Mass., USA). Mouse liver microsomes (Cat No. M1000, Lot No. 1310028) were obtained from Xenotech.

Working Solution of the Compounds and Other Solution

Compounds were dissolved in DMSO to make 10 mM stock solutions. 10 µL of the stock solution was diluted with acetonitrile (990 µL) to get a 100 µM working solution.

Incubation

Microsomes were preincubated with test compound for 10 min at 37° C. in 100 mM potassium phosphate buffer with pH 7.4. The reactions were initiated by adding NADPH regenerating system to give a final incubation volume of 200 µL and shaken in a water bath at 37° C. Incubation mixtures consisted of liver microsomes (0.5 mg microsomal protein/mL), substrates (1.0 µM), and NADP (1 mM), isocitric dehydrogenase(1 unit/mL), isocitric acid (6 mM).

Preparation of Samples for Analysis

At 30 min, reaction was quenched by adding 600 µL cold acetonitrile (including 100 ng/mL tolbutamide and 100 ng/mL labetalol as internal standard). The samples were centrifuged at 4000 rpm for 20 minutes and the resultant supernatants were subjected to LC-MS/MS analysis.

The samples for calibration curve were prepared as followed. Dispense 100 µL/well liver microsomes and 98 µL/well NADPH regenerating system solution to 96-well plate. Add 600 µL quenching solution first, and then followed by 2 µL Standard curve and QC working solution.

Bioanalysis

The compounds were quantified on an API4000 LC-MC/MC instrument in the ESI-Positive MRM mode.

A study was undertaken to evaluate the metabolic conversion of prodrugs (1 µM), Example 1 to 23 to the corresponding active forms, Compound 1a, Compound 3a, Compound 6a, Compound 8a, Compound 12a, Compound 14a, Compound 18a, Compound 20a, Compound 22a, in the presence of human liver microsomes. Results were summarized and shown in Table 2.

TABLE 2

Metabolic conversion of prodrugs in human liver microsomes

| Example No. | Corresponding Metabolized Product (active form) | Metabolized product concentration in human liver microsomes (µM) |
| --- | --- | --- |
| Example 1 | Compound 1a | 0.21 |
| Example 2 | Compound 1a | 0.42 |
| Example 3 | Compound 3a | 0.073 |
| Example 4 | Compound 3a | 0.21 |
| Example 5 | Compound 3a | 0.11 |
| Example 6 | Compound 6a | 0.49 |
| Example 7 | Compound 6a | 0.017 |
| Example 8 | Compound 8a | 0.67 |
| Example 9 | Compound 8a | 0.019 |
| Example 10 | Compound 8a | 0.008 |
| Example 11 | Compound 8a | 0.13 |
| Example 12 | Compound 12a | 0.13 |
| Example 13 | Compound 12a | 0.025 |
| Example 14 | Compound 14a | 0.21 |
| Example 15 | Compound 14a | 0.061 |
| Example 16 | Compound 14a | 0.041 |
| Example 17 | Compound 14a | 0.073 |
| Example 18 | Compound 18a | 0.88 |
| Example 19 | Compound 18a | 0.18 |
| Example 20 | Compound 20a | 0.144 |
| Example 21 | Compound 20a | 0.023 |
| Example 22 | Compound 22a | 0.2 |
| Example 23 | Compound 22a | 0.26 |

Example 26

Single dose PK study in Male Wister-Han Rats

The single dose PK in Male Wister-Han Rats was performed to assess pharmacokinetic properties of tested compounds. Two groups of animals were dosed via Gavage (POE) of the respective compound. Blood samples (approximately 20 µL) were collected via Jugular vein or an alternate site at 15 min, 30 min, 1 h, 2 h, 4 h, 7 h and 24 h post-dose groups. Blood samples were placed into tubes containing EDTA-K2 anticoagulant and centrifuged at 5000 rpm for 6 min at 4° C. to separate plasma from the samples. After centrifugation, the resulting plasma was transferred to clean tubes for bioanalysis of both prodrug and active form on LC/MS/MS. In the groups that prodrugs were dosed, the concentration of prodrugs in the plasma samples was under the detection limit. The "tested compound" in Table 3 was used as the internal standard for testing the metabolite (active form) of "dose compound" in vivo. The pharmacokinetic parameters were calculated using non-compartmental module of WinNonlin® Professional 6.2. The peak concentration (Cmax) was recorded directly from experimental observations. The area under the plasma concentration-time curve ($AUC_{0-5}$) was calculated using the linear trapezoidal rule up to the last detectable concentration.

$C_{max}$ and $AUC_{0\text{-}last}$ are two critical PK parameters related to the in vivo efficacy of the tested compound. Compounds with higher $C_{max}$ and $AUC_{0\text{-}last}$ will lead to the better in vivo efficacy. Results of PK parameters following oral administration of active forms and competitor compounds are given in Table 7. The PK parameters of prodrugs are tabulated in Table 3.

Following oral administration of prodrugs, the active forms were observed in plasma and therefore tested. The exemplified prodrugs of present invention (Example 8) surprisingly showed much improved $AUC_{0\text{-}last}$ (14.5 folds increase) comparing with compounds mentioned in present invention (Compound 8a) which is active forms. The results clearly demonstrated the unexpected superiority of prodrugs over active forms on PK parameters which led to better in vivo efficacy.

TABLE 3

PK parameters of prodrugs and active form after 5 mg/kg oral dosing

| Dose compound | Tested compound | $C_{max}$ (nM) | $AUC_{0\text{-}last}$ (nM · h) |
| --- | --- | --- | --- |
| Example 8 | Compound 8a | 621 | 3983 |
| Example 8a | Compound 8a | Not detected | 275 |

The invention claimed is:

1. A compound of formula (I),

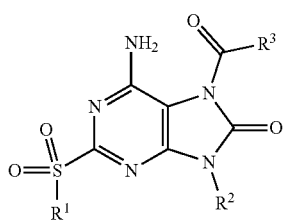

wherein:
R¹ is $C_{1-6}$alkyl;
R² is phenyl$C_{1-6}$alkyl, said phenyl being unsubstituted or substituted by one, two or three substituents independently selected from halogen, $C_{1-6}$ alkoxy and $C_{1-6}$alkyl; and
R³ is —NR⁴R⁵, wherein:
R⁴ and R⁵ are independently selected from $C_{1-6}$alkyl or $C_{1-6}$alkoxy$C_{1-6}$alkyl; or
R⁴ and R⁵ together with the nitrogen they are attached to form a heterocyclyl;
or a pharmaceutically acceptable salt, enantiomer or diastereomer thereof.

2. A compound according to claim 1, wherein:
R¹ is $C_{1-6}$alkyl;
R² is phenyl$C_{1-6}$alkyl, said phenyl being unsubstituted or substituted by halogen, $C_{1-6}$alkoxy or $C_{1-6}$ alkyl; and
R³ is pyrrolidinyl or —NR⁴R⁵, wherein R⁴ and R⁵ are independently selected from $C_{1-6}$alkyl or $C_{1-6}$alkoxy$C_{1-6}$alkyl;
or a pharmaceutically acceptable salt, enantiomer or diastereomer thereof.

3. A compound according to claim 1, wherein:
R¹ is ethyl or propyl;
R² is benzyl, bromobenzyl, chlorobenzyl, fluorobenzyl, methylbenzyl or methoxybenzyl; and
R³ is pyrrolidinyl, or —NR⁴R⁵, wherein R⁴ and R⁵ are independently selected from methyl, ethyl, propyl or methoxyethyl.

4. A compound according to claim 3, wherein R³ is pyrrolidinyl, methyl(ethyl)amino, methyl(propyl)amino, methyl(methoxyethyl)amino, or dimethylamino.

5. A compound according to claim 1, wherein R² is benzyl substituted by halogen or $C_{1-6}$ alkyl.

6. A compound according to claim 5, wherein R² is bromobenzyl, chlorobenzyl, fluorobenzyl or methylbenzyl.

7. A compound according to claim 5, wherein R² is bromobenzyl, chlorobenzyl or fluorobenzyl.

8. A compound according to claim 5, wherein:
R³ is —NR⁴R⁵, wherein R⁴ is $C_{1-6}$alkyl and R⁵ is $C_{1-6}$alkyl.

9. A compound according to claim 8, wherein R³ is methyl(propyl)amino or methyl(ethyl)amino.

10. A compound according to claim 1, wherein:
R¹ is $C_{1-6}$alkyl;
R² is benzyl, said benzyl being substituted by halogen or $C_{1-6}$alkyl; and
R³ is —NR⁴R⁵, wherein R⁴ is $C_{1-6}$alkyl, and R⁵ is $C_{1-6}$alkyl.

11. A compound according to claim 10, wherein:
R¹ is ethyl or propyl;
R² is bromobenzyl, chlorobenzyl or fluorobenzyl; and
R³ is methyl(propyl)amino or methyl(ethyl)amino.

12. A compound selected from:
6-amino-9-benzyl-N-ethyl-N-methyl-8-oxo-2-propyl sulfonyl-purine-7-carboxamide;
6-amino-9-benzyl-N-methyl-8-oxo-N-propyl-2-propyl sulfonyl-purine-7-carboxamide;
6-amino-9-benzyl-N-ethyl-2-ethylsulfonyl-N-methyl-8-oxo-purine-7-carboxamide;
6-amino-9-benzyl-2-ethylsulfonyl-N-methyl-8-oxo-N-propyl-purine-7-carboxamide;
6-amino-9-benzyl-2-ethylsulfonyl-7-(pyrrolidine-1-carbonyl)purin-8-one;
6-amino-9-[(4-chlorophenyl)methyl]-N-methyl-8-oxo-N-propyl-2-propylsulfonyl-purine-7-carboxamide;
6-amino-9-[(4-chlorophenyl)methyl]-N-ethyl-N-methyl-8-oxo-2-propylsulfonyl-purine-7-carboxamide;
6-amino-9-[(4-chlorophenyl)methyl]-2-ethylsulfonyl-N-methyl-8-oxo-N-propyl-purine-7-carboxamide;
6-amino-9-[(4-chlorophenyl)methyl]-N-ethyl-2-ethylsulfonyl-N-methyl-8-oxo-purine-7-carboxamide;
6-amino-9-[(4-chlorophenyl)methyl]-2-ethylsulfonyl-N,N-dimethyl-8-oxo-purine-7-carboxamide;
6-amino-9-[(4-chlorophenyl)methyl]-2-ethylsulfonyl-N-(2-methoxyethyl)-N-methyl-8-oxo-purine-7-carboxamide;
6-amino-N-methyl-8-oxo-N-propyl-2-propylsulfonyl-9-(p-tolylmethyl)purine-7-carboxamide;
6-amino-N-ethyl-N-methyl-8-oxo-2-propylsulfonyl-9-(p-tolylmethyl)purine-7-carboxamide;
6-amino-2-ethylsulfonyl-N-methyl-8-oxo-N-propyl-9-(p-tolylmethyl)purine-7-carboxamide;
6-amino-N,N-diethyl-2-ethylsulfonyl-8-oxo-9-(p-tolylmethyl)purine-7-carboxamide;
6-amino-N-ethyl-2-ethylsulfonyl-N-methyl-8-oxo-9-(p-tolylmethyl)purine-7-carboxamide;
6-amino-2-ethylsulfonyl-9-(p-tolylmethyl)-7-(pyrrolidine-1-carbonyl)purin-8-one;
6-amino-2-ethylsulfonyl-9-[(4-fluorophenyl)methyl]-N-methyl-8-oxo-N-propyl-purine-7-carboxamide;
6-amino-N-ethyl-2-ethylsulfonyl-9-[(4-fluorophenyl)methyl]-N-methyl-8-oxo-purine-7-carboxamide;
6-amino-9-[(4-methoxyphenyl)methyl]-N-methyl-8-oxo-N-propyl-2-propylsulfonyl-purine-7-carboxamide;
6-amino-N-ethyl-9-[(4-methoxyphenyl)methyl]-N-methyl-8-oxo-2-propylsulfonyl-purine-7-carboxamide;
6-amino-9-[(4-bromophenyl)methyl]-2-ethylsulfonyl-N-methyl-N-propyl-8-oxo-purine-7-carboxamide; and
6-amino-9-[(4-bromophenyl)methyl]-N-ethyl-2-ethylsulfonyl-N-methyl-8-oxo-purine-7-carboxamide;
or a pharmaceutically acceptable salt, enantiomer or diastereomer thereof.

13. A pharmaceutical composition comprising a compound in accordance with claim 1 and a therapeutically inert carrier.

14. A process for preparing a compound according to claim 1, the process comprising:
reacting a compound of formula (II),

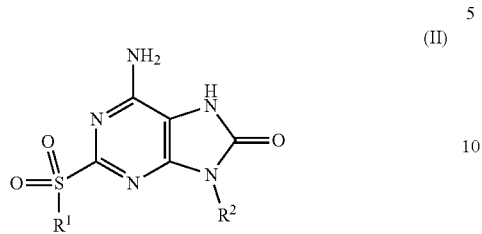

(II)

with carbamoyl chloride in the presence of a mixed base; wherein the mixed base is pyridine and triethylamine, pyridine and DIPEA, DMAP and triethylamine, or DMAP and DIPEA, wherein $R^1$ is $C_{1-6}$alkyl and $R^2$ is phenyl$C_{1-6}$alkyl, said phenyl being unsubstituted or substituted by one, two or three substituents independently selected from halogen, $C_{1-6}$alkyl and $C_{1-6}$alkoxy.

* * * * *